(12) United States Patent
Ilan

(10) Patent No.: US 8,586,564 B2
(45) Date of Patent: *Nov. 19, 2013

(54) SYNTHETIC GLYCOLIPID ANALOGUES AND DERIVATIVES FOR THE TREATMENT OF PATHOLOGIC DISORDERS

(75) Inventor: Yaron Ilan, Givat Massua (IL)

(73) Assignee: Enzo Therapeutics, Inc., Farmingdale, NY (US)

( * ) Notice: Subject to any disclaimer, the term of this patent is extended or adjusted under 35 U.S.C. 154(b) by 82 days.
This patent is subject to a terminal disclaimer.

(21) Appl. No.: 12/586,100

(22) Filed: Sep. 17, 2009

(65) Prior Publication Data

US 2010/0093649 A1    Apr. 15, 2010

Related U.S. Application Data

(63) Continuation-in-part of application No. 10/675,980, filed on Sep. 30, 2003.

(51) Int. Cl.
| | | |
|---|---|---|
| A01N 43/04 | (2006.01) | |
| A61K 31/70 | (2006.01) | |
| C07G 3/00 | (2006.01) | |
| C07G 11/00 | (2006.01) | |
| C07H 15/00 | (2006.01) | |
| C07H 17/00 | (2006.01) | |

(52) U.S. Cl.
USPC .............. 514/62; 514/25; 514/886; 514/909; 536/4.1

(58) Field of Classification Search
USPC ................. 514/62, 25, 866, 909; 536/4.1
See application file for complete search history.

(56) References Cited

U.S. PATENT DOCUMENTS

| | | | |
|---|---|---|---|
| 6,756,504 B2 * | 6/2004 | Dagan et al. | 554/52 |
| 7,897,580 B2 * | 3/2011 | Ilan | 514/25 |
| 2003/0170258 A1 | 9/2003 | Roy-Chowdhury et al. | |
| 2007/0117778 A1 * | 5/2007 | Ilan | 514/54 |
| 2009/0221516 A1 * | 9/2009 | Tashiro et al. | 514/25 |

FOREIGN PATENT DOCUMENTS

| | | |
|---|---|---|
| WO | WO 01/79152 A1 * | 10/2001 |
| WO | WO03/027058 | 4/2003 |
| WO | WO2005/032462 | 4/2005 |
| WO | WO2007/060652 | 5/2007 |
| WO | WO 2007/099999 A1 * | 9/2007 |

OTHER PUBLICATIONS

"Immunodeficiency Disorders" from the Merck Manual Home Edition [online]. [Retrieved Mar. 18, 2011]. Retrieved from the Internet <http://www.merckmanuals.com/home/print/sec16/ch184/ch184a.html>.*
"Immune System" from KidsHealth [online]. [Retrieved Mar. 24, 2011]. Retrieved from the internet <http://kidshealth.org/teen/your_body/body_basics/immune.html> Published Jun. 18, 2007.*
Mackay, I.R., Rosen, F.S. (2001) Autoimmune Diseases, New England Journal of Medicine, vol. 345, No. 5, p. 340-350.*
"Neurological disorders" from health-cares.net [online], [retrieved Jan. 6, 2010]. Retrieved from the internet <http://neurology.health-cares.net/>, published online Feb. 7, 2005.*
"Degenerative nervous system diseases" from health-cares.net [online], [retrieved Jan. 6, 2010]. Retrieved from the internet <http://neurology.health-cares.net/degenerative-system.php>, published online Jun. 26, 2005.*
Merck Manual Home Edition, subject "Viral Infections" [online], [Retrieved on Oct. 16, 2008]. Retrieved from the internet <http://www.merck.com/mmhe/print/sec17/ch198/ch198a.html>.*
Todar, K. (2008) "Bacterial Resistance to Antibiotics" in Todar's Online Textbook of Bacteriology, [online], [Retrieved on Dec. 28, 2008]. Retrieved from the internet <http://www.textbookofbacteriology.net/resantimicrobial.html>, p. 1-4.*
Gatenby, R.A., Gawlinski, E.T. (2003) The Glycolytic Phenotype in Carcinogenesis and Tumor Invasion: Insights through Mathematical Models. Cancer Research, vol. 63, p. 3847-3854.*
Hoffman, E.P. (2000) "Genetic Changes in Cancer: Second of Three Parts" [online], [Retrieved on Apr. 14, 2011]. Retrieved from the internet <http://www.candlelighters.org/Research/genetics2.aspx>.*
Motoki, K., Morita, M., Kobayashi, E., Uchida, T., Akimoto, K., Fukushima, H., Koezuka, Y. (1995) Immunostimulatory and Antitumor Activities of Monoglycosylceramides Having Various Sugar Moieties. Biological and Pharmaceutical Bulletin, vol. 18, No. 11, p. 1487-1491.*
Collins et al., RAG1, RAG2 and pre-T cell receptor alpha chain expression by adult human hepatic T cells: evidence for extrathymic T cell maturation, Eur. J. Immunol. 1996, 3114-3118, 26.
Epstein et al., The SCID-hu myeloma model, Methods in Molecular Medicine, 2005, 183-90, 113.
Hotamisligil et al., Adipose expression of tumor necrosis factor—alpha:direct role in obesity-linked insulin resistance, Science 1993, 87-91, 259.
Madsen et al., Interleukin 10 prevents cytokine-induced disruption of T84 monolayer barrier integrity and limits chloride secretion, Gastroenterology, 1997, 151-159, 133.
Mayeux , R., Epidemiology of neurodegeneration, Annu. Rev. Neurosci. 2003, 81-104, 26.
Mitchell et al.,Chemical shift phase-difference and suppression magnetic resonance imaging techniques in animals, phantoms, and humans, Invest. Radiol. 1991, 1041-1052, 26.
Namimoto et al., Adrenal Masses: quantification of fat content with double-echo chemical sHift in-phase and opposed-phase FLASH MR images for differentiation of adrenal adenomas, Radiology, 2001, 642-646, 218.
Selkoe, D., Alzheimer's disease: genes, proteins, and therapy, Physiological Reviews, 2001, 741-766, 81.
Trop et al., Liver-associated lymphocytes expressing NK1.1 are essential for oral immune tolerance induction in a murine model, Hepatology, 1999, 746-755, 27.
Vanderkerken, et al., The 5T2MM murine model of multiple myeloma, Methods of Mol. Med., 2005, 191-205, 113.
Weiner, H., Oral tolerance: immune mechanisms and treatment of autoimmune diseases, Immunol. Today, 1997, 335-343, 18.

* cited by examiner

*Primary Examiner* — Scarlett Goon
(74) *Attorney, Agent, or Firm* — Anna D. DiGabriele Petti, Esq

(57) ABSTRACT

The present invention describes compositions and methods for synthetic analogues and derivatives of β-glycolipids. These analogues and derivatives may be used for the treatment, amelioration or prevention of a pathological disorder. They may also be used for the modulation of the Th1/Th2 cell balance toward an anti-inflammatory or pro-inflammatory response, resulting in the treatment, amelioration or prevention of immune-related disorders.

16 Claims, 5 Drawing Sheets

SYNTHETIC GLYCOLIPID ANALOGUES AND DERIVATIVES FOR THE TREATMENT OF PATHOLOGIC DISORDERS

REFERENCE TO RELATED PATENT APPLICATIONS

This application is a continuation-in-part of the patent application entitled "Glucocerebroside Treatment of Disease," application Ser. No. 10/675,980, filed on Sep. 30, 2003.

FIELD OF THE INVENTION

The invention relates to the use of synthetic derivatives of β-glycolipids as immunomodulators. More particularly, the invention relates to the use of synthetic derivatives of β-glycolipids, preferably, the compounds of any one of Formula I, II, III and IV or any mixture or combination thereof for the treatment of different pathologic disorders, particularly, immune-related disorders and neurodegenerative disorders.

BACKGROUND OF THE INVENTION

All publications mentioned throughout this application are fully incorporated herein by reference, including all references cited therein.

Immune therapy involves the exposure of components of the immune system to various elements (cytokines, disease associated antigens and natural metabolites) to combat disease processes in which a dysregulated immune response is thought to play a role. Immune dysregulation is thought to play a major part in the pathogenesis or disease course of a great number of disease processes, including various neoplastic, inflammatory, infectious and genetic entities.

These disorders can be perceived as a dysbalance between pro-inflammatory (Th1) and anti-inflammatory (Th2) cytokines, and few of them are described herein below.

The role of the immune system in the pathogenesis of inflammatory bowel disease Inflammatory bowel diseases (IBD) are common gastrointestinal disorders, that can be perceived as being the result of a dysbalance between Th1-pro-inflammatory, and Th2-anti-inflammatory subtypes of immune responses.

There are several extra-intestinal manifestations that accompany IBD, for example: autoimmune phenomena; immune complexes have a role in target organ damage; and, immunosuppressive agents such as glucocorticoids, azathioprine, methotrexate and cyclosporin are used to alleviate the disease. Patients with IBD have antibodies against components of colon cells and several different bacterial antigens. These antigens gain access to the immune system as a consequence of epithelial damage. Abnormalities of T cell-mediated immunity, including coetaneous anergy and diminished responsiveness to T cell stimuli, have also been described in these patients. In addition, changes in mucosal cell mediated immunity were identified, including increased concentrations of mucosal IgG cells and changes in T cells subsets, suggesting antigen stimulation. Exposure of target antigens after infectious, immune, or toxic damage, leads to activation of mucosal immune cells resulting in cytokines that lead to mucosal inflammatory response. Secretion of pro-inflammatory cytokines such as IFNγ, contributes to an increase in mucosal permeability, and has been described in animal models of IBD. Similarly, an increase in collagen synthesis mediated by IL1 and IL6 can be detected in these animals. A Th1-mediated granulomatous colitis model has been established by the adoptive transfer of normal CD45RB T cells from Balb/C mice into CB-17 scid mice. CD4 cells from CD45RB were shown to prevent the disease when injected together with the CD45RB population. This prevention could be reversed by adding antibodies to TGFβ1.

The Th1/Th2 Dysbalance in Inflammatory Bowel Disease

Both CD4 and CD8 lymphocytes can be typed as either Th1 cells that produce IL-2 and IFNγ, or Th2 cells that produce IL-4, and IL-10. The way the immune system responds to foreign and self antigens, is the result of a balance between the two subtypes of responses. A Th1 type response is involved in the pathogenesis of several autoimmune and chronic inflammatory disorders such as IBD. Thus experimental colitis and IBD in humans can be perceived as a dysbalance between pro-inflammatory Th1-type and anti-inflammatory Th2-type cytokines. It has been recently shown, in both animals and humans, that anti-inflammatory cytokines such as IL-10 can downregulate the pro-inflammatory effects of Th1-mediated cytokines, thereby alleviating immune-mediated disorders.

The Role of the Immune System in the Pathogenesis of Non-Alcoholic Steatohepatitis Non-alcoholic steatohepatitis (NASH) is a clinico-pathological entity consisting of hepatic fat accumulation, inflammation and fibrosis in patients who have no history of alcohol consumption. It may progress to cirrhosis in 20% of cases and is considered the most common cause of cryptogenic cirrhosis in the Western world. NASH is common in patients who suffer of other metabolic disturbances, which are suggested to play a contributing role in the pathogenesis of the disorder. These include insulin resistance, obesity-related ATP depletion, increased free-fatty-acid beta peroxidation, iron accumulation, antioxidant depletion, and leptin deficiency. Yet no therapeutic intervention, including weight loss, tight diabetic control, normalization of lipid levels and antioxidant treatment have consistently shown an alteration in the natural progression of the disorder.

Most information about NASH has been derived from two mammalian models: leptin-deficient ob/ob mice and leptin-receptor deficient fa/fa Zucker rats. Leptin is a protein that is involved with the regulation of body weight. Its deficiency in rodents and humans results in a severe form of 'metabolic syndrome' (formerly termed syndrome X) consisting of morbid obesity, glucose intolerance, hyperlipidemia, and severe hepatic steatosis. Yet, as mentioned above, no intervention aimed at correcting some of these metabolic disturbances have resulted in an amelioration of the hepatic steatosis, fibrosis, and inflammation.

Recent evidence suggests that the immune system may play a pivotal role in the pathogenesis of NASH in the leptin deficient models. In leptin deficient mice, defective hepatic macrophage (Kupffer cell) response has been observed after liver injury induction by lipopolysaccharide. In similar models, LPS induction of IL6 was greatly enhanced, while that of IL10 was inhibited. Ob/ob mice hepatic macrophages were observed to produce more IL12 and less IL15 than control mice in response to LPS challenge, which may explain the significant reduction in the number and function of NKT lymphocytes observed in these mice. Other observations have shown a reduction in the number of CD4 T lymphocytes in the blood and liver of leptin-deficient ob/ob mice. This may explain the relative resistance of leptin-deficient mice to Concanavalin A hepatitis, which is mediated by CD4 T lymphocytes.

The Th1/Th2 Dysbalance in Non-Alcoholic Steatohepatitis

CD4 and CD8 lymphocytes are classified as either Th1 cells that produce IL-2 and IFNγ, or Th2 cells that produce IL-4 and IL-10. The immune system responds to foreign and self-antigens by a shift in balance between the two subtypes of responses [Weiner, H. L. et al., Immunol. Today 18: 335-343 (1997)]. Usually the Th1 type response causes a pro-inflammatory reaction, while anti-inflammatory cytokines such as IL10 shift the balance towards an anti-inflammatory Th2 reaction, thereby alleviating immune-mediated disorders. NKT cells, in response to different endogenous and exogenous stimuli, are believed to play a major role in the direction of the immune system towards either the Th1 or Th2 pathways.

Leptin has been shown to play a major role in the immune regulation of the balance between Th1 and Th2 response. In the leptin-deficient ob/ob mice NASH model an alteration of the number and function of NKT cells has been suggested to tilt the immune system towards the Th1 response. This is suggested to result in an increased sensitivity to LPS induced hepatotoxicity and a unique resistance to the hepatotoxic effects of Concanavalin A. The difference may be in their different pathogenic mechanisms. The former depends upon the action of the innate hepatic immune system, which is hyperactive in the leptin-deficient mice, while the latter is dependent upon the activation of NKT-lymphocytes, which are suppressed and defective in the leptin deficient mice.

The Immune System and Obesity

The immune system and the regulation of adipose tissue metabolism appear to be closely interlinked. Up to fifty percent of cells within adipose tissues are composed of non-adipose cells, including many immunocytes. Most research has been focused on the immunological consequences of morbid obesity. Immunological alterations which are known to exist in obese animals and humans include reduced DTH and mitogen-stimulated lymphocyte proliferation responses, impaired phagocyte number and function, attenuation of insulin induced lymphocyte cytotoxicity, and changes in the CD4/CD8 ratio, especially during weight loss attempts.

Adipose cells are known to secrete pro-inflammatory cytokines including TNF-β [Hotamisligil, G. S. et al., Science 259:87-91 (1993)] and IL6, which are both related to the level of adiposity. Some of these cytokines are considered to have metabolic effects such as insulin resistance mediated by TNF-β and lipoprotein lipase inhibition mediated by IL6. TNF-βknockout mice have higher insulin sensitivity and improved lipid profile than their normal littermates. Other components of the immune system, which are produced by adipose cells, include the protein adipsin, which is an integral part of the alternative complement system, and functions identically to human complement factor D.

Little information is known about the role of the immune system as a mediator of obesity, but several recent studies suggest that the immune system may have an important contributory role in the development of obesity. Several cytokines are known to act as adipose tissue regulators. TNF-β suppresses the expression of $β_3$ adreno-receptors on adipose cells, which are involved in sympathetically mediated lipolysis, while IL1 stimulates adipose leptin secretion. The metabolic activity rate of adipose cells has been observed to be closely correlated to their distance from the closest lymph node, through a mechanism which is partly mediated by IL4, IL6 and TNF-β.

These observations, which point to the fact that obese animals and humans may also be suffering of various alterations in the different arms of the immune system, suggest that modulation of the immune system may change some of the pathogenic mechanisms responsible for the development of morbid obesity.

Neurodegenerative disorders, which are chronic and progressive, are characterized by selective and symmetric loss of neurons in motor, sensory, or cognitive systems. Delineation of the patterns of cell loss and the identification of disease-specific cellular markers have aided in nosologic classification, senile amyloid plaques (SP), neurofibrillary tangles (NFT), neuronal loss, and acetylcholine deficiency define Alzheimer's disease (AD), Lewy bodies and depletion of dopamine characterize Parkinson's disease, cellular inclusions and swollen motor axons are found in amyotrophic lateral sclerosis, and γ-aminobutyric acid-containing neurons of the neostriatum are lost in Huntington's disease.

It is well accepted that the intrinsic differences in cellular metabolism of distinctive brain regions and neuronal populations underlie the selective cellular response to various environmental neurotoxicants, and neuropathological conditions, therefore causing distinct neurodegenerative diseases.

Amyloid diseases are caused by the misfolding of proteins into structures that lead them to cluster together, forming microscopic fibril or plaques, which deposit in internal organs and interfere with normal function, sometimes lethally.

These diseases include Alzheimer's disease, Parkinson's disease, and the peripheral nervous system disease familial amyloid polyneuropathy (FAP). In Alzheimer's disease, these clumps are termed amyloid plaques and consist primarily of the amyloid-beta (Aβ) peptide. In the case of Alzheimer's disease, these fibrils cause degeneration of nerve cells in areas of the brain that are crucial for memory. The Aβ peptides possess neurotoxic properties also in their soluble form. In Parkinson disease, they are called Lewy bodies and contain the protein α-synuclein. FAP, a collection of more than 80 rare amyloid diseases are caused by the misfolding of the protein transthyretin (TTR), which the liver secretes into the bloodstream to carry thyroid hormone and vitamin A.

In the FAP diseases, mutations in the TTR protein are known to play a direct role in causing the disease. These changes alter protein folding in such a way as to predispose the proteins to misfold and accumulate into microscopic fibrils, which can grow into protein plaques.

In Alzheimer's disease, the cause of misfolding is not so obvious. A number of mutations are associated with rare forms of familial Alzheimer's disease, but not with most common cases (about 95 percent of the cases). This suggests there must be a more common cause of Alzheimer's disease.

Traumatic head injuries are a major risk factor for later developing Alzheimer's disease. The body responds to such injuries with inflammatory reactions that cause the release of components of lipid membranes, such as cholesterol. Inflammation can lead to the production of reactive oxygen species such as ozone, which can trigger pathological changes in other molecules in the body, like cholesterol.

Alzheimer's disease (AD) is a progressive neurodegenerative incurable disease. It is the major cause of dementia in the elderly. The estimated number of patients is approximately 20 million worldwide and is expected to keep growing as the world population ages. In the USA, an estimated 10% of Americans over the age of 65 and half of these over 85 have AD.

The onset of the disease is characterized by impaired memory but with disease progression other intellectual skills decline. Later, erratic behavior, delusions and a loss of control over body functions occur. The major brain pathological features include the senile amyloid plaques (SP), composed of Aβ peptide, and the neurofibrillary tangles (NFT), which are aggregations of the hyperphosphorylated microtubular protein tau.

Cholinergic dysfunction as well as oxidative stress are implicated in the disease pathogenesis. As these cellular changes progress, neurons are lost in the hippocampus, entorhinal cortex, and association areas of the neocortex [reviewed in Mayeux R. (2003) Annu. Rev. Neurosci. 26:81-104; Selkoe D. (2001) Physiological Rev. 81:741-766].

The etiology of AD is complex and involves a combination of factors including genetic, immune, endocrine and environmental factors. One such AD-related factor that is attracting recently great attention is the role of cholesterol metabolism and trafficking. There is accumulating data in support of the hypothesis that altering in the cholesterol levels influences the development of AD by affecting the formation of Aβ peptide, its distribution within cholesterol rich membranes and its fibrillogenesis.

Parkinson's disease (PD) is the second most common neurodegenerative disorder after Alzheimer's disease, with a prevalence of two percent among people over the age of 65 years. The disease is mostly sporadic, but familial forms are recognized as well. Parkinson disease (PD) targets dopaminergic neurons in the substantia nigra, resulting in motor disturbances such as resting tremor, bradykinesia, and rigidity. There is a substantial clinical overlap between Alzheimer's disease and Parkinson's disease. Dementia develops in approximately 20 to 30 percent of patients with Parkinson's disease, and the brains of these patients often contain Lewy bodies, SP and NFT.

The third common neurodegenerative diseases are the motor neuron diseases. The most common motor-neuron disorder is amyotrophic lateral sclerosis (ALS), which usually begins in the fifth and sixth decades of life. The illness is usually sporadic, but in 1 to 10 percent of patients it is familial, being inherited as an autosomal dominant trait. In a typical patient, muscles innervated by both brain stem and spinal cord atrophy as lower motor neurons die, although those that control eye movements and bowel and bladder function are spared. The prognosis is grave, with death occurring in three to five years in 95 percent of patients.

Another neurodegenerative disease is the Huntington's disease, which is an autosomal dominant disorder with high penetrance. The characteristic findings of progressive chorea and dementia are caused by severe neuronal loss, initially in the neostriatum and later in the cerebral cortex.

Although the regions and cells that degenerate in these various illnesses and insults are distinct, several features are common to many of these conditions and include aberrant protein interactions and aggregation, mitochondrial dysfunction, altered antioxidant defenses, oxidative stress, inflammation and apoptosis.

Different neurological disorders, known as "taupathies" have been recently described. In these disorders it has been suggested that modifications in the microtubule-associated protein tau could cause neural degeneration in specific regions. Although these regions are different in the different taupathies, some common features appear to occur in all of them: neurofibrillary tangles (NFT), which are aggregations of the abnormal hyperphosphorylated microtubular protein tau.

Abnormal tau proteins are often seen as mechanisms that can lead to brain degeneration in Alzheimer's disease and other neurodegenerative disorders known as taupathies. In all taupathies, there are neuropathologic aggregates of paired helical filaments and/or straight filaments composed of aberrantly phosphorylated tau proteins in central nervous system neurons or glia.

Although impressive advances in understanding of these diseases have been made, still the mechanisms of brain degeneration are not resolved, and no effective drug is available. To date only the secondary degenerative effects have been amenable to therapy.

WO 2005/032462, which is a previous publication by the present inventors, discloses the general use of intermediary metabolites and preferably, glucocerebrosides, in the treatment of immune-related disorders. The inventors have further showed recently that β-lactosyl-ceramide may be used as a preferred β-glycolipid for immune-modulation (IL2006/001217). The inventors further demonstrated a clear synergistic effect of a particular combination of two β-glycolipids, preferably a mixture of β-lactosyl-ceramide (LC) with β-glucosylceramide (GC), which may be used as a powerful medicament for the treatment of immune-related disorders.

Still further, the inventors recently demonstrated the use of β-glycolipids, particularly GC and LC, in the treatment of neurodegenerative disorders and CNS related inflammatory autoimmune disorders.

In another publication, WO03/027058, the present inventors disclosed synthetic sphingolipid derivatives, particularly for use in treating lipid storage diseases.

The present invention now clearly demonstrates the use of synthetic derivatives of β-glycolipids, and particularly of the compounds of Formulas I, II, III and IV, for the treatment of pathologic disorders.

It is therefore an object of the invention to provide novel synthetic derivatives of β-glycolipids, as well as compositions thereof and methods for treating pathologic disorders such as immune-related disorders and neurodegenerative disorders.

These and other objects of the invention will become clearer as the description proceeds.

SUMMARY OF THE INVENTION

In a first aspect, the invention relates to synthetic derivatives of β-glycolipids, more particularly, the invention relates to a compound of Formula I, or isomer thereof or a pharmaceutically acceptable salt thereof, Formula I being:

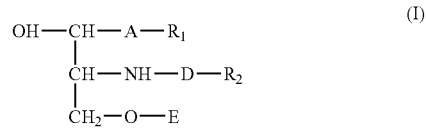

wherein
A represents alkenylene or alkylene bivalent radical selected from CH=CH— and —CH(OH)—CH$_2$—;
D represents a bivalent radical selected from —CSNH—, —CONH—, —CS—, and —SO$_2$—;
E represents a glycosyl radical selected from glucosyl, galactosyl, sulfated galactosyl, manosyl, and lactosyl;
R$_1$ is a linear C$_{8-21}$ alkyl; and
R$_2$ is a univalent radical selected from linear or branched alkyl or alkenyl chains optionally substituted with hydroxyl, adamantanyl, and norbornenyl. In one embodiment, A in said Formula I is —CH=CH—. In other embodiment, E in said formula I is glucosyl. $R_1$ in said Formula I may be $C_{10-16}$alkyl, for example $C_{13}$alkyl. In other embodiment of the invention, said $R_2$ in said formula I is selected from linear $C_{6-18}$alkyl and adamantanyl. Said glycosyl in Formula I is preferably β-glycosyl.

According to one embodiment, the compound of the invention may be the compound of Formula II, also designated as AD2897, or isomer thereof or a pharmaceutically acceptable salt thereof. Formula II being:

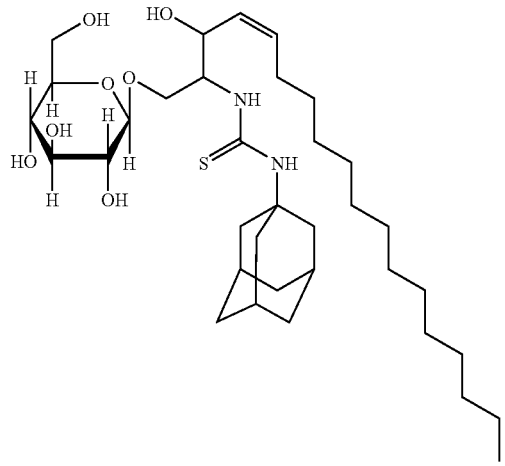

(II)

According to another embodiment, the compound of the invention may be the compound of Formula III, also designated as AD2898, or a pharmaceutically acceptable salt thereof. Formula III being:

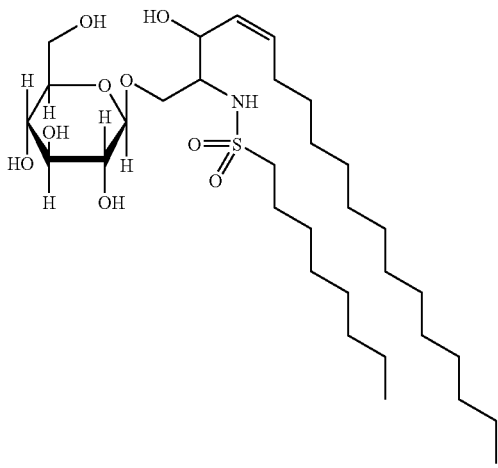

(III)

In a further preferred embodiment, the compound of the invention may be the compound of Formula IV, also designated as AD2899, or a pharmaceutically acceptable salt thereof.

Formula IV being:

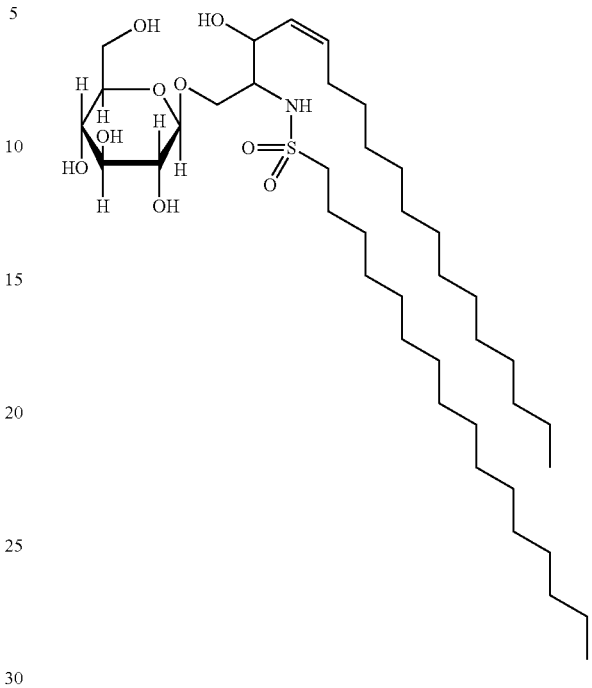

(IV)

In a second aspect, the invention relates to a composition comprising at least one of the compounds of any one of Formula I, II, III and IV. The composition of the invention may further comprise at least one of a pharmaceutically acceptable carrier, diluent, excipient and/or additive.

According to a third aspect, the invention relates to a therapeutic composition for the treatment, amelioration, or prevention of a pathologic disorder in a mammalian subject. More particularly, the therapeutic composition of the invention may comprise as an active ingredient any one of: (a) at least one of the compounds of Formula I, II, III and IV; (b) a mixture of at least two compounds of Formula I, II, III and IV; (c) educated NKT cells pre-exposed to at least one of the compounds of Formula I, II, III and IV, or to any mixture or any combination thereof; and (d) any combinations of (a), (b) and (c). It should be noted that the therapeutic composition of the invention may optionally further comprises at least one of a pharmaceutically acceptable carrier, diluent, excipient and/or additive.

In a further aspect, the invention provides a composition for the modulation of the Th1/Th2 cell balance toward an anti-inflammatory or pro-inflammatory response. Such composition comprises as an active ingredient an immunomodulatory effective amount of any one of: (a) at least one of the compounds of Formula I, II, III and IV; (b) a mixture of at least two compounds of any one of Formula I, II, III and IV; (c) educated NKT cells pre-exposed to at least one of the compounds of Formula I, II, III and IV, or to any mixture or any combination thereof; and (d) any combinations of (a), (b) and (c).

According to a fifth aspect, the invention provides a method for the treatment, amelioration, or prevention of a pathologic disorder in a mammalian subject in need thereof. The method of the invention comprises the step of administering to the treated subject a therapeutically effective amount of any one of: (a) at least one compound of Formula I, II, III and IV; (b) a mixture of at least two compounds of Formula I, II, III and IV; (c) at least one component of the treated subject's immune-system which was pre-exposed to an effective amount of at least one of the compounds of any one of Formula I, II, III and IV, or to any mixture or any combination thereof; (d) a composition comprising any one of (a), (b) and (c) or (e) any combination of (a), (b), (c) and (d).

According to another aspect, the invention provides a method for modulating the Th1/Th2 cell balance toward an anti-inflammatory or pro-inflammatory response in a subject in need thereof. The method of the invention comprises the step of administering to the treated subject a therapeutically effective amount of any one of: (a) at least one compound of Formula I, II, III and IV; (b) a mixture of at least two compounds of Formula I, II, III and IV; (c) at least one component of the treated subject's immune-system which was pre-exposed to an effective amount of at least one of the compounds of Formula I, II, III and IV, or to any mixture or any combination thereof; (d) a composition comprising any one of (a), (b) and (c) or (e) any combination of (a), (b), (c) and (d).

Still further, the invention provides a method for the preparation of a medicament for the treatment of a pathologic disorder or condition in a subject in need thereof comprising the steps of: (A) providing an immunomodulatory compound comprising any one of: (a) at least one of the compounds of Formula I, II, III and IV; (b) a mixture of at least two compounds of Formula I, II, III and IV; (c) educated NKT cells pre-exposed to at least one of the compounds of Formula I, II, III and IV, or to any mixture or any combination thereof or any combinations thereof and (B) admixing the immunomodulatory compound provided in step (A) with a pharmaceutically acceptable carrier.

According to a further aspect, the invention relates to the use of a therapeutically effective amount of at least one of a compounds of Formula I, II, III and IV, or any combinations and mixtures thereof, in the preparation of a pharmaceutical composition for the treatment or prevention of a pathologic disorder in a subject in need thereof. More preferably, the use according to the invention is of a compound of Formula I, II, III and IV as defined by the invention.

These and other aspects of the invention will become apparent by the hand of the following figures and examples.

DETAILED DESCRIPTION OF THE INVENTION

Figure 1:
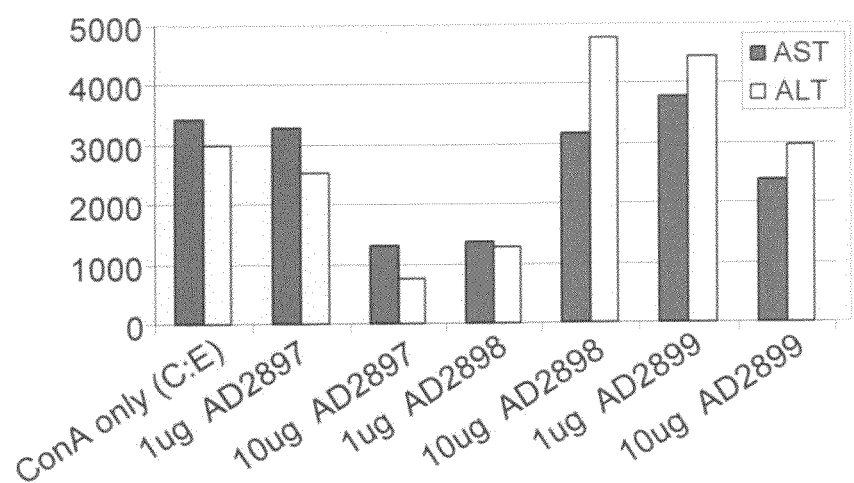
FIG. 1 Effect of administration of the three synthetic analogs of the invention AD2897, AD2898, and AD2899 (1 µg or 10 µg/mice) upon liver function in a ConA induced hepatitis model, as reflected by AST (aspartate aminotransferase), black bars, and ALT (alanine aminotransferase), open bars.

In a first aspect, the invention relates to synthetic derivatives of β-glycolipids, more particularly, the invention relates to a compound of Formula I, or isomer thereof or a pharmaceutically acceptable salt thereof:

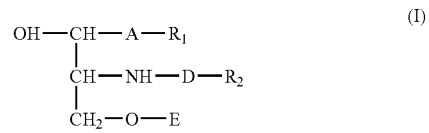

wherein
A represents alkenylene or alkylene bivalent radical selected from —CH=CH— and —CH(OH)—CH$_2$—;
D represents a bivalent radical selected from —CSNH—, —CONH—, —CS—, and —SO$_2$—;
E represents a glycosyl radical selected from glucosyl, galactosyl, sulfated galactosyl, manosyl, and lactosyl;
R$_1$ is a linear C$_{8-21}$alkyl; and
R$_2$ is a univalent radical selected from linear or branched alkyl or alkenyl chains optionally substituted with hydroxyl, adamantanyl, and norbornenyl.

According to one embodiment, the compound of the invention may be the compound of Formula II, also designated as AD2897, or isomer thereof or a pharmaceutically acceptable salt thereof.

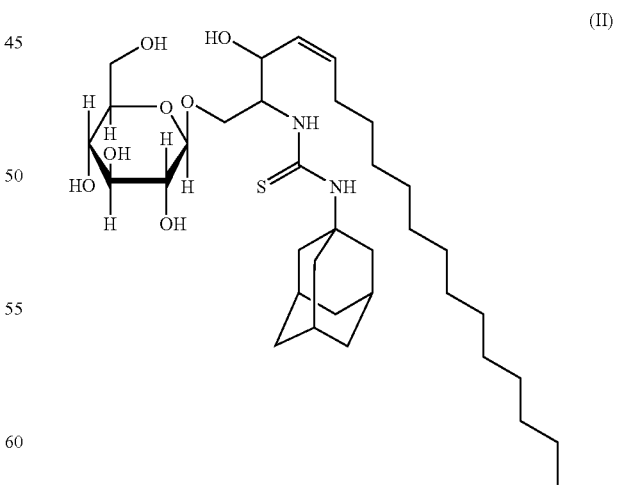

According to another embodiment, the compound of the invention may be the compound of Formula III, also designated as AD2898, or a pharmaceutically acceptable salt thereof.

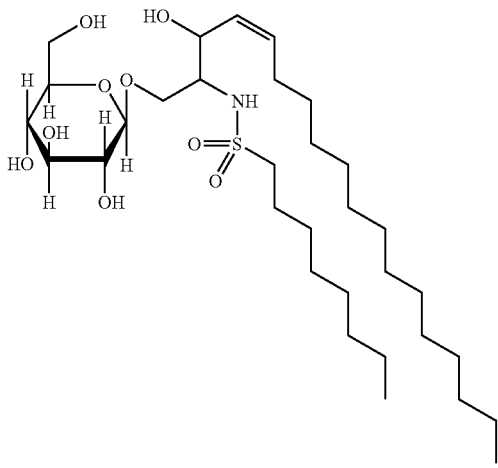

(III)

In a further preferred embodiment, the compound of the invention may be the compound of Formula IV, also designated as AD2899, or a pharmaceutically acceptable salt thereof.

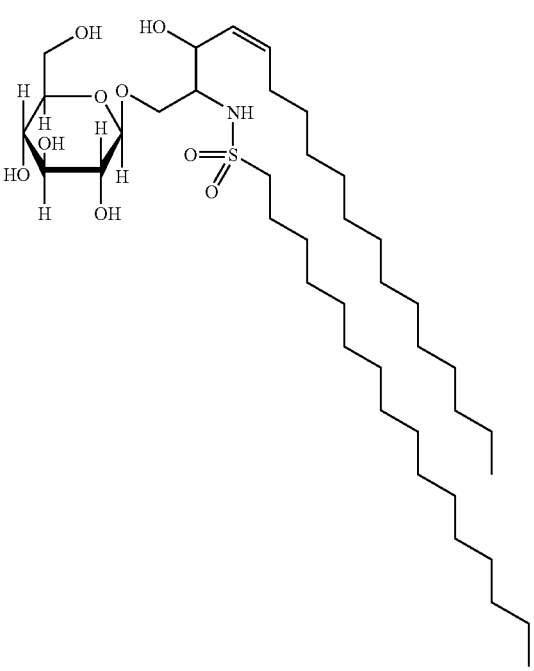

(IV)

As indicated above, the invention relates to the compounds of Formulas I, II, III and IV, which are the preferred synthetic derivatives of β-glycolipids. As indicated throughout the application, β-glycolipid or a natural β-glycolipid, is meant any compound selected from the group consisting of a monosaccharide ceramide, a glucosylceramide, a galatosyl-ceremide, a lactosyl-ceramide, a gal-gal-glucosyl-ceramide, GM2 ganglioside, GM3 ganglioside, globoside or any other β-glycolipid.

In a second aspect, the invention relates to a composition comprising the compound of Formula I. The composition of the invention may further comprise at least one of a pharmaceutically acceptable carrier, diluent, excipient and/or additive.

In one preferred embodiment, the composition of the invention comprises as an active ingredient the compound of Formula II, also referred to as AD2897. The composition of the invention may optionally further comprises at least one of a pharmaceutically acceptable carrier, diluent, excipient and/or additive.

According to another embodiment, the composition of the invention comprises as an active ingredient the compound of Formula III, also referred to as AD2898. It should be noted that the composition of the invention may further comprises at least one of a pharmaceutically acceptable carrier, diluent, excipient and/or additive.

In yet another embodiment, the composition of the invention comprises as an active ingredient the compound of Formula IV, also referred to as AD2899. It should be noted that the composition of the invention may further comprises at least one of a pharmaceutically acceptable carrier, diluent, excipient and/or additive.

Thus, the invention provides a composition comprising as an active ingredient at least one of the compounds as defined by the invention and may optionally further comprises at least one of a pharmaceutically acceptable carrier, diluent, excipient and/or additive.

According to a third aspect, the invention relates to a therapeutic composition for the treatment, amelioration, or prevention of a pathologic disorder in a mammalian subject. More particularly, the therapeutic composition of the invention may comprise as an active ingredient any one of: (a) at least one of the compounds of Formula I, II, III or IV; (b) a mixture of at least two compounds of Formula I, II, III or IV; (c) educated NKT cells pre-exposed to any one of the compounds of Formula I, II, III or IV, or to any mixture or any combination thereof; and (d) any combinations of (a), (b) and (c). It should be noted that the therapeutic composition of the invention may optionally further comprises at least one of a pharmaceutically acceptable carrier, diluent, excipient and/or additive.

In a further aspect, the invention provides a composition for the modulation of the Th1/Th2 cell balance toward an anti-inflammatory or pro-inflammatory response. Such composition comprises as an active ingredient an immunomodulatory effective amount of any one of: (a) At least one of the compounds of Formula I, II, III or IV; (b) a mixture of at least two compounds of Formula I, II, III or IV; (c) educated NKT cells pre-exposed to any one of the compounds of Formula I, II, III or IV, or to any mixture or any combination thereof; and (d) any combinations of (a), (b) and (c).

According to a specifically preferred embodiment, the compounds of Formula I, II, III or IV, comprised as an active ingredient in the therapeutic and immunomodulatory compositions of the invention are as defined by the invention.

According to one preferred embodiment, the therapeutic and immunomodulatory compositions of the invention may comprises a mixture of at least two of the compounds of Formula I, II, III or IV, or at least one of the compounds of Formula I, II, III or IV and any other synthetic or natural β-glycolipid derivatives at a quantitative ratio between 1:1 to 1:1000.

It should be appreciated that any quantitative ratio may be used. As a non-limiting example, a quantitative ratio used may be: 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:200, 1:300, 1:400, 1500, 1:750, 1:1000. It should be further noted that where the mixture of the invention comprises more than two synthetic derivatives of β-glycolipids, the quantitative ratio used may be for example, 1:1:1, 1:2:3, 1:10:100, 1:10:100:1000 etc.

In another specific embodiment, the mixture of said compounds may comprise the compound of Formula I and at least one of the compounds of any one of Formula II, III, IV, or any other synthetic or natural derivative of β-glycolipid, at a quantitative ratio between 1:1 to 1:1000.

Another specific embodiment relates to a mixture of said compounds which specifically comprises the compound of Formula II and at least one of the compounds of any one of Formula I, III, IV, or any other synthetic or natural derivative of β-glycolipid, at a quantitative ratio between 1:1 to 1:1000.

In yet another specific embodiment, the mixture of said compounds comprises the compound of Formula III and at least one of the compounds of any one of Formula I, II, IV or any other synthetic or natural derivative of β-glycolipid, at a quantitative ratio between 1:1 to 1:1000.

Another specific embodiment relates to a mixture of said compounds which specifically comprises the compound of Formula IV and at least one of the compounds of any one of Formula I, II, III, or any other synthetic or natural derivative of β-glycolipid, at a quantitative ratio between 1:1 to 1:1000.

According to one specifically preferred embodiment, the therapeutic and the immunomodulatory compositions of the invention are particularly intended for the treatment of a pathologic disorder such as an immune-related disorder and a neurodegenerative disorder.

More specifically, the therapeutic and the immunomodulatory compositions of the invention are capable of modulating the Th1/Th2 cell balance towards Th1 pro-inflammatory cytokine producing cells, and may therefore be intended for the treatment of any one of malignant and non-malignant proliferative disorder, genetic disease, bacterial infections, viral infections, fungal infections, or parasitic infections.

According to this embodiment, the therapeutic composition and the immunomodulatory compositions of the invention may be for the treatment of a malignant proliferative disorder such as solid and non-solid tumor. More particularly, such tumors may be carcinoma, sarcoma, melanoma, leukemia and lymphoma. Even more particularly, said solid and non-solid tumors may be any one of hepaotcellular carcinoma, melanoma, colon cancer, myeloma, acute and chronic leukemia.

In another specifically preferred embodiment, the therapeutic and the immunomodulatory compositions of the invention are capable of modulating the Th1/Th2 cell balance towards Th2 anti-inflammatory cytokine producing cells, and may therefore be intended for the treatment of any one of an autoimmune disease, graft rejection pathology, inflammatory disease, metabolic syndrome, immune mediated hepatitis, or neurodegenerative disorder.

According to this embodiment, the therapeutic and the immunomodulatory compositions of the invention are intended for the treatment of autoimmune disease such as rheumatoid arthritis, diabetes, asthma, acute and chronic graft versus host disease, systemic lupus erythmatosus, scleroderma, multiple sclerosis, non alcoholic fatty liver disease, hyperlipidmia, atherosclerosis, any part of the metabolic syndrome, overweight (obesity), inflammatory bowel disease and immune mediated hepatitis.

According to a specifically preferred embodiment the therapeutic and the immunomodulatory compositions of the invention may be particularly suitable for treating immune mediated hepatitis.

In yet another embodiment, the compositions of the invention are particularly suitable for the treatment of a neurodegenerative disorder such as a protein misfolding disorder, an amyloid disease, a CNS autoimmune disease, taupathy or a prion disease. More particularly, said neurodegenerative disorder may be any one of Alzheimer's disease, Parkinson's disease, ALS (Amyotrophic Lateral Sclerosis), Huntington's disease, Pick's disease, fronto temporal dementia, corticobasal degeneration, progressive supranuclear palsy, Spongiform encephalopathies, Scrapie, mad cow disease and Bovine spongiform encephalopathy, Creutzfeldt-Jakob disease, Fatal Familial Insomnia, Gerstmann-Straussler-Scheinker syndrome and Kuru.

Another particular embodiment relates to the therapeutic and the immunomodulatory compositions of the invention which further comprises NK T cells. According to this embodiment, educated NK T cells are capable of modulating the Th1/Th2 cell balance toward an anti-inflammatory or pro-inflammatory response. More particularly, such educated NK T cells may be, prior to their administration to the treated subject, cultured or "educated" in the presence of any one of: (a) at least one of the compounds of Formula I, II, III, IV or a mixture of at least two compounds of Formula I, II, III, IV or any combination thereof; (b) combination of (a) with antigens associated with the treated pathologic disorder; (c) combination of (a) with at least one of liver-associated cells of tolerized or non-tolerized subject suffering from said pathologic disorder or of said subject; (d) combination of (a) with at least one of cytokines, adhesion molecules and any combination thereof; (e) combination of (a) with antigen presenting cells; and (f) a combination of any of (b), (c), (d) and (e).

According to one preferred embodiment, said education of NK T cells may result in the modulation of the Th1/Th2 cell balance toward Th2 anti-inflammatory cytokine producing cells.

The NK T cell that has been ex vivo educated may also be comprised within the compositions of the invention and therefore may be re-introduced to the treated subject. This can be carried out by a process that has been termed adoptive transfer. The particular educated NK T cells used for the transfer may preferably originate from the subject (autologous transfer). A syngeneic or non-syngeneic donor (non-autologous transfer) is not excluded. The storage, growth or expansion of the transferred cells may have taken place in vivo, ex vivo or in vitro.

Cell therapy may be by injection, e.g., intravenously, or by any of the means described herein above. Neither the time nor the mode of administration is a limitation on the present invention. Cell therapy regimens may be readily adjusted taking into account such factors as the possible cytotoxicity of the educated cells, the stage of the disease and the condition of the patient, among other considerations known to those of skill in the art.

It is to be appreciated that the NK T cells used by the compositions of the invention may be educated in vivo as well, via any of the methods described above, they can be modulated prior to or at any point of time following exposure to the synthetic derivatives of β-glycolipids as defined by the invention, antigens or any other component described.

According to another preferred embodiment, said education of NK T cells may result in the modulation of the Th1/Th2 cell balance toward Th1 pro-inflammatory cytokine producing cells. According to this embodiment the educated NK T cells used for the compositions of the invention may be intended for the treatment of malignant and non-malignant proliferative disorder, bacterial infections, viral infections, fungal infections, or parasitic infections.

It should be noted that the therapeutic composition of the invention may optionally further comprises at least one of a pharmaceutically acceptable carrier, diluent, excipient and/or additive.

According to another embodiment, the therapeutic and immunomodulatory compositions of the invention may optionally further comprises another active ingredient which may be any one of: (a) antigens associated with the specific pathologic disorder to be treated; (b) at least one of liver-associated cells of tolerized or non-tolerized subjects suffering from the treated pathologic disorder or of the subject to be treated (autologous cells); (c) at least one of cytokines, adhesion molecules or any combination thereof; (d) antigen presenting cells; and (e) a combination of any of (a), (b), (c) and (d).

More specifically, antigens associated with said pathologic disorder to be treated may be for example, any one of allogeneic antigens obtained from a donor subject suffering from said immune-related disorder, xenogenic antigens, syngeneic antigens, autologous antigens, non-autologous antigens and recombinantly prepared antigens and any combinations thereof. These antigens can be native or non-native with regards to the subject. They can be natural or synthetic, modified or unmodified, whole or fragments thereof. Fragments can be derived from synthesis as fragments or by digestion or other means of modification to create fragments from larger entities. Such antigen or antigens comprise but are not limited to proteins, glycoproteins, enzymes, antibodies, histocompatibility determinants, ligands, receptors, hormones, cytokines, cell membranes, cell components, viruses, viral components, viral vectors, non-viral vectors, whole cells, tissues or organs. The antigen can consist of single molecules or mixtures of diverse individual molecules. The antigen can present itself within the context of viral surface, cellular surface, membrane, matrix, or complex or conjugated with a receptor, ligand, antibody or any other binding partner.

Polymerization and degradation, fractionation and chemical modification are all capable of altering the properties of a particular antigen in terms of potential immune responses. These small segments, fragments or epitopes can either be isolated or synthesized.

The compositions of the present invention further encompass the use of recombinantly prepared antigens. Preparation of recombinant antigens involves the use of general molecular biology techniques that are well known in the art. Such techniques include for example, cloning of a desired antigen to a suitable expression vector.

According to another embodiment, liver-associated cells may be for example Kupffer cells, Stellate cells, liver endothelial cells liver associated stem cells or any other liver-related lymphocytes.

The use of peripheral lymphocytes from tolerized or non-tolerized patients suffering from the same immune-related disorder or from the treated subject, is also contemplated in the present invention. In order to obtain lymphocytes from a subject, particularly human subject, blood is drawn from the patient by cytopheresis, a procedure by which a large number of white cells are obtained, while other blood components are being simultaneously transferred back to the subject.

In another particular embodiment, cytokines such as IL4, IL10, TGFβ, IFNγ, IL12 and IL15, or adhesion molecules such as Integrins, Selectin and ICAM may also be included in the composition of the invention.

The preparation of pharmaceutical compositions is well known in the art and has been described in many articles and textbooks, see e.g., Remington's Pharmaceutical Sciences, Gennaro A. R. ed., Mack Publishing Co., Easton, Pa., 1990, and especially pp. 1521-1712 therein, fully incorporated herein by reference.

The pharmaceutical composition of the invention can be administered and dosed in accordance with good medical practice. Administration may be carried out in various ways, including intravenous, intraperitoneal, intramuscular or subcutaneous injection. However, other methods of administration such as nasal or oral administration are also contemplated by the invention.

The composition of the invention may comprise the active substance in free form and be administered directly to the subject to be treated. Formulations typically comprise at least one active ingredient, as defined above, together with one or more acceptable carriers thereof. Each carrier should be both pharmaceutically and physiologically acceptable in the sense of being compatible with the other ingredients and not injurious to the patient.

As indicated above, Formulations include those suitable for oral, nasal, or parenteral (including subcutaneous (s.c.), intramuscular (i.m.), intraperitoneal (i.p.), intravenous (i.v.) and intradermal administration. The Formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

The pharmaceutical forms suitable for injection use include sterile aqueous solutions or dispersions and sterile powders for the extemporaneous preparation of sterile injectable solutions or dispersions. In all cases the form must be sterile and must be fluid to the extent that easy syringe ability exists. The compositions must be stable under the conditions of manufacture and storage and must be preserved against the contaminating action of microorganisms, such as bacteria and fungi.

In many cases, it will be preferable to include isotonic agents, for example, sugars or sodium chloride. Prolonged absorption of the injectable compositions can be brought about by the use in the compositions of agents delaying absorption.

In the case of sterile powders for the preparation of the sterile injectable solutions, the preferred method of preparation are vacuum-drying and freeze drying techniques which yield a powder of the active ingredient plus any additional desired ingredient from a previously sterile-filtered solution thereof.

The pharmaceutical compositions of the invention generally comprise a buffering agent, an agent that adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

In instances in which oral administration is in the form of a tablet or capsule, the active drug components can be combined with a non-toxic pharmaceutically acceptable inert carrier such as lactose, starch, sucrose, glucose, modified sugars, modified starches, methylcellulose and its derivatives, dicalcium phosphate, calcium sulfate, mannitol, sorbitol, and other reducing and non-reducing sugars, magnesium stearate, stearic acid, sodium stearyl fumarate, glyceryl behenate, calcium stearate and the like. For oral administration in liquid form, the active drug components can be combined with non-toxic pharmaceutically acceptable inert carriers such as ethanol, glycerol, water and the like. When desired or required, suitable binders, lubricants, disintegrating agents and coloring and flavoring agents can also be incorporated into the mixture. Stabilizing agents such as antioxidants, propyl gallate, sodium ascorbate, citric acid, calcium metabisulphite, hydroquinone, and 7-hydroxycoumarin can also be added to stabilize the dosage forms. Other suitable compounds can include gelatin, sweeteners, natural and synthetic gums such as acacia, tragacanth, or alginates, carboxymethylcellulose, polyethylene, glycol, waxes and the like.

Alternatively, the composition of this invention may also be administered in controlled release formulations such as a slow release or a fast release Formulation. Such controlled release formulations of the combination of this invention may be prepared using methods well known to those skilled in the art. The method of administration will be determined by the attendant physician or other person skilled in the art after an evaluation of the subject's conditions and requirements.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art. Methods of preparing various pharmaceutical compositions with a certain amount of active ingredient are known, or will be apparent in light of this disclosure, to those skilled in this art.

According to a fifth aspect, the invention provides a method for the treatment, amelioration, or prevention of a pathologic disorder in a mammalian subject in need thereof. The method of the invention comprises the step of administering to the treated subject a therapeutically effective amount of any one of: (a) at least one of the compounds of Formula I, II, III or IV; (b) a mixture of at least two compounds of Formula I, II, III or IV; (c) at least one component of the treated subject's immune-system which was pre-exposed to an effective amount of any one of the compounds of Formula I, II, III or IV, or to any mixture or any combination thereof; (d) a composition comprising any one of (a), (b) and (c) or (e) any combination of (a), (b), (c) and (d).

According to another aspect, the invention provides a method for modulating the Th1/Th2 cell balance toward an anti-inflammatory or pro-inflammatory response in a subject in need thereof. The method of the invention comprises the step of administering to the treated subject a therapeutically effective amount of any one of: (a) at least one of compound of Formula I, II, III or IV; (b) a mixture of at least two compounds of Formula I, II, III or IV; (c) at least one component of the treated subject's immune-system which was pre-exposed to an effective amount of any one of the compounds of Formula I, II, III or IV, or to any mixture or any combination thereof; (d) a composition comprising any one of (a), (b) and (c) or (e) any combination of (a), (b), (c) and (d).

It should be noted that compound of Formula I, II, III or IV used by the methods of the invention are as defined by the invention.

According to one embodiment, a mixture of the compounds of Formula I, II, III or IV used by the methods of the invention may comprises at least two of the compounds of Formula I, II, III, IV or any β-glycolipid derivatives at a quantitative ratio between 1:1 to 1:1000.

According to one specific embodiment, the mixture used by the methods of the invention preferably comprises the compound of Formula I and at least one of the compounds of any one of Formula II, III, IV or any other synthetic or natural derivative of β-glycolipid, at a quantitative ratio between 1:1 to 1:1000.

According to another specific embodiment, the mixture used by the methods of the invention preferably comprises the compound of Formula II and at least one of the compounds of any one of Formula I, III, IV or any other synthetic or natural derivative of β-glycolipid, at a quantitative ratio between 1:1 to 1:1000.

According to another specific embodiment, the mixture used by the methods of the invention preferably comprises the compound of Formula III and at least one of the compounds of any one of Formula I, II, IV or any other synthetic or natural derivative of β-glycolipid, at a quantitative ratio between 1:1 to 1:1000.

In another specific embodiment, the mixture used by the methods of the invention preferably comprises the compound of Formula IV and at least one of the compounds of any one of Formula I, II, III or any other synthetic or natural derivative of β-glycolipid, at a quantitative ratio between 1:1 to 1:1000.

According to one particular embodiment, the methods of the invention comprises the step of administering to the treated subject a therapeutically effective amount of at least one component of the treated subject's immune-system which was pre-exposed to an effective amount of any one of the compounds of Formula I, II, III or IV, or to any mixture or any combination thereof. According to this embodiment, a component of the treated subject's immune-system may be selected from the group consisting of cellular immune reaction elements, humoral immune reaction elements and cytokines. Preferably, such cellular immune reaction element may be a population of NKT cells.

More specifically, according to this embodiment, such NK T cells were exposed to an effective amount of any one of a compound of Formula I, II, III or IV, or to any mixture or any combination thereof. The exposure of the NK T cells may be performed by the steps of: (a) obtaining NK T cells from said subject, or from a non autologous subject; (b) ex vivo educating the NK T cells obtained in step (a) such that the resulting educated NK T cells modulate the Th1/Th2 cell balance toward an anti-inflammatory or pro-inflammatory cytokine producing cells; and (c) re-introducing to said subject the educated NK T cells obtained in step (b) which modulate the Th1/Th2 cell balance toward Th2 anti-inflammatory cytokine producing cells.

The ex vivo education of such NK T cells is as described herein before for the therapeutic and the immunomodulatory compositions of the invention.

According to another embodiment, the methods of the invention are suitable for the treatment of a pathologic disorder such as an immune-related disorder or a neurodegenerative disorder.

As used herein, the term "disorder" or "condition" refers to a condition in which there is a disturbance of normal functioning. A "disease" is any abnormal condition of the body or mind that causes discomfort, dysfunction, or distress to the person affected or those in contact with the person. Sometimes the term is used broadly to include injuries, disabilities, syndromes, symptoms, deviant behaviors, and atypical variations of structure and function, while in other contexts these may be considered distinguishable categories. It should be noted that the terms "disease", "disorder", "condition" and "illness", are equally used herein.

According to a specifically preferred embodiment, the methods of the invention are capable of modulating the Th1/Th2 cell balance towards Th1 pro-inflammatory cytokine producing cells, and may be applicable for the treatment of any one of malignant and non-malignant proliferative disorder, genetic disease, bacterial infections, viral infections, fungal infections, or parasitic infections.

As used herein to describe the present invention, "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the methods and compositions of the present invention may be used in the treatment of non-solid and solid tumors.

Malignancy, as contemplated in the present invention may be for example, carcinoma, melanoma, lymphoma, leukemia and sarcoma. Malignancies that may find utility in the present invention can comprise but are not limited to hematological malignancies (including leukemia, lymphoma and myeloproliferative disorders), hypoplastic and aplastic anemia (both virally induced and idiopathic), myelodysplastic syndromes, all types of paraneoplastic syndromes (both immune mediated and idiopathic) and solid tumors (including lung, liver, breast, colon, prostate GI tract, pancreas and Karposi). More particularly, the malignant disorder may be hepaotcellular carcinoma, colon cancer, melanoma, myeloma, acute or chronic leukemia.

According to a particular embodiment, the viral infection treated by the methods and compositions of the invention, may be caused by any one of HBV, HCV or HIV.

In another specifically preferred embodiment, the methods of the invention are capable of modulating the Th1/Th2 cell balance towards Th2 anti-inflammatory cytokine producing cells, and are intended for the treatment of any one of an autoimmune disease, graft rejection pathology, inflammatory disease, metabolic syndrome, immune mediated hepatitis, or neurodegenerative disorder.

According to this embodiment, the methods of the invention are intended for treating an autoimmune disease. Non-limiting examples for an autoimmune disease include rheumatoid arthritis, diabetes, asthma, acute and chronic graft versus host disease, systemic lupus erythmatosus, scleroderma, multiple sclerosis, non alcoholic fatty liver disease, hyperlipidemia, atherosclerosis, any part of the metabolic syndrome, overweight, inflammatory bowel disease, immune mediated hepatitis.

According to a specifically preferred embodiment the methods of the invention may be particularly suitable for treating immune mediated hepatitis.

In another specific embodiment, the methods of the invention are intended for the treatment of a neurodegenerative disorder such as a protein misfolding disorder, an amyloid disease, a CNS autoimmune disease, taupathy or a prion disease.

A "neurological disorder" is a disease or disorder characterized by an abnormality or malfunction of neuronal cells or neuronal support cells. The disorder can affect the central and/or peripheral nervous system. Exemplary neurological diseases include neuropathies, skeletal muscle atrophy and neurodegenerative diseases.

"Neurodegenerative disorders" are complex and pernicious diseases, their onset is insidious, followed by progressive deterioration. Clinical manifestations are determined by the location and seriousness of the disorder. Although the causes may differ, patients with neurodegenerative disorders are likely to show localized to generalized atrophy of brain cells, leading to compromises in both mental and physical function. Exemplary neurodegenerative diseases include: Alzheimer's disease, Parkinson's disease, ALS (Amyotrophic Lateral Sclerosis), Huntington's disease, taupathies such as Pick's disease, fronto temporal dementia, cortico-basal degeneration and progressive supranuclear palsy and Spongiform encephalopathies such as Scrapie, mad cow disease and Bovine spongiform encephalopathy, Creutzfeldt-Jakob disease, Fatal Familial Insomnia, Gerstmann-Straussler-Scheinker syndrome and Kuru.

Mentally, patients will exhibit forgetfulness, poor memory, decrease in mental capacities, emotional disturbances, and/or poor speech. Physically, patients will exhibit partial to complete incontinence, aspiration of food particles, tremor, poor balance, muscle rigidity, and/or muscle paralysis.

The terms "Amyloid disease", "Amyloid condition" or "Amyloidosis" refers to deposits of proteins causing diseases. Occasionally, cells produce abnormal proteins that can settle in body tissue, forming deposits and causing disease. The deposits of abnormal proteins are called amyloids, and the disease process amyloidosis.

"Prion diseases" often called "spongiform encephalopathies", are a group of progressive conditions that affect the brain and nervous system of humans and animals. The disorders cause degenerative diseases of the nervous system reflected by impairment of brain function, including memory changes, personality changes, and problems with movement that worsen over time. Probably most mammalian species develop these diseases. The infectious agent causing the diseases has been called a prion. A "prion" has been defined as a small proteinaceous infectious particle which resists inactivation by procedures that modify nucleic acids. Prions are microscopic protein particles similar to a virus but lacking nucleic acid, capable of self-reproducing. Though their exact mechanisms of action and reproduction are still unknown, it is accepted that they are responsible for a number conditions in humans, Creutzfeld-Jacob Disease (CJD), Gerstmann-Straussler-Scheinker syndrome (GSS), Fatal Familial Insomnia (FFI), Kuru, Alpers Syndrome; and in cattle (livestock), Scrapie in sheep, transmissible mink encephalopathy (TME) in mink, chronic wasting disease (CWD) in mule deer or elk, and bovine spongiform encephalopathy (BSE) in cows.

Abundant cytoplasmic inclusions consisting of aggregated hyperphosphorylated protein tau, called neurofibrillary tangles (NFT), are a characteristic pathological observation in several neurodegenerative disorders, known as taupathies. These disorders include Alzheimer's disease, Pick's disease, frontotemporal dementia, cortico-basal degeneration and progressive supranuclear palsy.

According to a specifically preferred embodiment, the methods of the invention are specifically suitable for the treatment of a mammalian subject. "Mammal" or "mammalian" for purposes of treatment refers to any animal classified as a mammal including, human, research animals, domestic and farm animals, and zoo, sports, or pet animals, such as dogs, horses, cats, cows, etc. In a particular embodiment said mammalian subject is a human subject.

The terms "treat, treating, treatment" as used herein and in the claims mean ameliorating one or more clinical indicia of disease activity in a patient having a pathologic disorder.

"Treatment" refers to therapeutic treatment. Those in need of treatment are mammalian subjects suffering from any pathologic disorder By "patient" or "subject in need" is meant any mammal for which administration of the synthetic β-glycolipid derivatives of the invention which are preferably any one of the compounds of Formula I, II, III or IV, any combination thereof or any pharmaceutical composition comprising this compound, is desired in order to prevent, overcome or slow down such infliction.

To provide a "preventive treatment" or "prophylactic treatment" is acting in a protective manner, to defend against or prevent something, especially a condition or disease.

It should be noted that for the method of treatment and prevention provided in the present invention, said therapeutic effective amount, or dosage, is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. In general, dosage is calculated according to body weight, and may be given once or more daily, weekly, monthly or yearly, or even once every 2 to 20 years. Persons of ordinary skill in the art can easily estimate repetition rates for dosing based on measured residence times and concentrations of the composition of the invention in bodily fluids or tissues. Following successful treatment, it may be desirable to have the patient undergo maintenance therapy to prevent the recurrence of the disease state, wherein the composition of the invention is administered in maintenance doses, once or more daily.

According to another embodiment, the synthetic β-glycolipid derivatives used by the methods of the invention or any mixture or combination thereof may administered alone, or in combination with other active ingredient/s that improve the therapeutic effect, whether administered in combination, serially or simultaneously.

The methods of the invention involve administration of effective amount of the active ingredient to a subject in need thereof. The terms "effective amount" or "sufficient amount" mean an amount necessary to achieve a selected result. The "effective treatment amount" is determined by the severity of the disease in conjunction with the preventive or therapeutic objectives, the route of administration and the patient's general condition (age, sex, weight and other considerations known to the attending physician).

Therapeutic and immunomodulatory Formulations may be administered in any conventional dosage Formulation. Formulations typically comprise at least one active ingredient, as defined above, together with one or more acceptable carriers thereof.

Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The Formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

In yet another embodiment, the administration step according to the methods of the invention includes oral, intravenous, intramuscular, subcutaneous, intraperitonea, perenteral, transdermal, intravaginal, intranasal, mucosal, sublingual, topical, rectal or subcutaneous administration, or any combination thereof.

The invention further provides a method for protection of neuronal cells from a neurodegenerative process comprising the step of contacting said cells with a neuroprotective effective amount of any one of a compound of Formula I, II, III, IV, or any mixture or any combination thereof, a composition comprising the same or any combinations thereof.

A "neuroprotective effect" is aimed to prevent and treat complications that might result in central nervous system (CNS) damage. Neuroprotection can be estimated by parameters of cell survival or cell death delay, arrest or slowing of the disease progression, disease onset and disease mortality delay.

Neuroprotective agents usually interact with the cell survival/apoptotic machinery. Products with neuroprotective effects include those from the categories of free radical scavengers, anti-excitotoxic agents, apoptosis (programmed cell death) inhibitors, anti-inflammatory agents, neurotrophic factors, metal ion chelators, ion channel modulators and gene therapy.

Neuroprotective therapies are usually directed to cerebrovascular disorders, traumatic brain injury, spinal cord injury, Alzheimer's disease, Parkinson's disease, amyotrophic lateral sclerosis, Huntington's disease, taupathies, multiple sclerosis, epilepsy and ischemic optic neuropathy.

Still further, the invention provides a method for the preparation of a medicament for the treatment of a pathologic disorder in a subject in need thereof comprising the steps of: (A) providing an immunomodulatory compound comprising any one of: (a) at least one of the compounds of Formula I, II, III or IV, a mixture of at least two compounds of Formula I, II, III or IV, educated NKT cells pre-exposed to any one of the compounds of Formula I, II, III or IV, or to any mixture or any combination thereof and (B) admixing the immunomodulatory compound provided in step (A) with a pharmaceutically acceptable carrier.

According to a further aspect, the invention relates to the use of a therapeutically effective amount of any one of a compounds of Formula I, II, III, IV, or any combinations and mixtures thereof, in the preparation of a pharmaceutical composition for the treatment or prevention of a pathologic disorder in a subject in need thereof. More preferably, the use according to the invention is of a compound of Formula I, II, III or IV, as defined by the invention.

In another embodiment, the use according to the invention may be wherein the pathologic disorder is any one of an immune-related disorder and a neurodegenerative disorder.

The invention further provides the use of the immunomodulatory composition according to the invention as a supporting medicament for the treatment of immune-related disorders and neurodegenerative disorder.

The invention further provides a diagnostic method for predicting responsiveness of a subject suffering from a pathologic disorder to treatment with synthetic or natural derivatives of β-glycolipids. The diagnostic method of the invention is based on monitoring the direct or indirect modulations in structure and composition of a cell membrane obtained from the tested subject in response to treatment with the synthetic or natural derivatives of β-glycolipids. This diagnostic method comprises the steps of: (a) obtaining cells from the tested subject; (b) exposing these cells to an effective amount of a compounds of Formula I, II, III, IV, or any combinations and mixtures thereof under suitable conditions; and (c) identifying an alteration in the membrane composition and structure of said cells, as compared to a control, by a suitable means. Wherein an alteration in the membrane composition and structure of the cells as compared to a control is indicative of responsiveness of said subject to treatment with said synthetic or natural derivative of glycolipids.

By predicting the responsiveness of the particular tested subject to a certain synthetic derivatives of β-glycolipids, in a certain concentration or mixture thereof, the diagnostic method of the invention provides a "tailor-made" treatment, personally adjusted and adapted for each specific patient.

It should be further appreciated that the diagnostic method of the invention may also be used for follow-up of treated patients.

According to one embodiment, the cells obtained from the tested subject may be any one of microglial cells, NKT lymphocyte, dendritic cell, any regulatory lymphocyte, and type of lymphocyte.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

DESCRIPTION OF THE PREFERRED EMBODIMENTS

Materials and Methods

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., Molecular cloning: A laboratory manual, Cold Springs Harbor Laboratory, New-York (1989, 1992), and in Ausubel et al., Current Protocols in Molecular Biology, John Wiley and Sons, Baltimore, Md. (1988).

Standard organic synthesis protocols known in the art not specifically described herein are generally followed essentially as in Organic syntheses: Vol. 1-79, editors vary, J. Wiley, New York, (1941-2003); Gewert et al., Organic synthesis workbook, Wiley-VCH, Weinheim (2000); Smith & March, Advanced Organic Chemistry, Wiley-Interscience; 5th edition (2001).

Standard medicinal chemistry methods known in the art not specifically described herein are generally followed essentially as in the series "Comprehensive Medicinal Chemistry", by various authors and editors, published by Pergamon Press.

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Vanderkerken K The 5T2MM murine model of multiple myeloma: maintenance and analysis. [Methods Mol. Med. 113:191-205 (2005); Epstein J. The SCID-hu myeloma model. Methods Mol. Med. 113:183-90 (2005)].

Animals
  Normal inbred 2 to 4 month old C57Bl/6 male mice are obtained from Harlan laboratories.
  Normal inbred 2 to 4 month old Balb/C male mice are obtained from Harlan laboratories.
  Ten-week-old male leptin-deficient C57BL/6J mice and lean C57BL/6 mice are purchased from Harlan laboratories.
  Eight week old male C57/bl mice are obtained from Jackson Laboratories (Bar Harbor, Me., USA).
  Male Sprague-Dawley rats (weighing 250-270 g), purchased from Harlan Laboratories Israel, are used as a PD model.
  14-15 weeks old transgenic mice expressing the human G93A SOD1 (B6SJL-TgN[SOD1-G93A]1Gur, purchased from Jackson Laboratory), are used as a model showing ALS related clinical symptoms.
  Transgenic mice model expressing a mutation in the amyloid precursor protein (APP) and in the presenilin1 gene is used as AD model. These tg mice present amyloid plaques starting at 9 months of age (purchased from Jackson Laboratory).
  C57Bl mice, purchased from Harlan Laboratories Israel, immunized with MOG.
  SJL/j mice immunized with PLP are purchased from Harlan Laboratories Israel.
  The sand rat *Psammomys obesus*), are purchased from the Jerusalem colony were purchased from Harlan laboratories (Jerusalem, Israel).
  Diabetic Cohen rats are purchased from the Jerusalem colony were purchased from Harlan laboratories (Jerusalem, Israel).
  All animals are maintained in the Animal Core of the Hadassah-Hebrew University Medical School. Mice are administered standard laboratory chow and water ad libitum, and kept in 12-hour light/dark cycles. Animal experiments were carried out according to the guidelines of the Hebrew University-Hadassah Institutional Committee for Care and Use of Laboratory Animals, and with the committee's approval.

Neurotoxins
  Aβ (25-35) peptide purchased from Sigma.
  Cholesterol purchased from Sigma.

3-NP purchased from Sigma.
MPTP purchased from Sigma.
6OHDA purchased from Sigma.
Glutamate purchased from Sigma.

Induction of Con A Hepatitis

ConA (MP Biomedical, OH, USA) was dissolved in buffer containing 50 mM Tris, pH 7, 150 mM NaCl, and 4 mM $CaCl_2$, and then administered to each mouse by injection into the tail vein at a dose of 15 mg/kg, or 500 µg/mouse, in 100 µL.

FACS of Intrahepatic and Intrasplenic Lymphocytes for NKT, CD4 and CD8 Markers

Immediately following lymphocyte isolation, flow cytometry was performed on a 100 µL PBS sample containing $1 \times 10^6$ lymphocytes. Analysis of lymphocyte subpopulations was performed using PE-anti-mouse NK1.1, PE-Cy5 anti-mouse CD2, PE-anti-mouse CD4 and PE-anti-mouse CD-8 antibodies (eBioscience, CA, USA). The isolated lymphocytes were incubated for 30 min at 4° C. in the dark, then washed and resuspended in 200 µL PBS. For the oncol group, only 5 µl of 1% BSA was added. Analytical cell sorting was performed on $1 \times 10^4$ cells from each group with a fluorescence-activated cell sorter (FACSTAR plus, Becton Dickinson). Only live cells were counted and background fluorescence from non-antibody-treated lymphocytes was deducted from the levels obtained. Gates were set on forward- and side-scatters to exclude dead cells and red blood cells. The data were analyzed with Consort 30 two-color contour plot program using the BD CELLQuest 25™ software program (Becton Dickinson, Oxnard, Calif.).

Measurement of Cytokine Levels

Blood is drawn from mice in all groups and centrifuged at 14,000 rpm. Serum IFNγ, IL2, IL4, IL10 and IL-12 levels are measured by "sandwich" ELISA using commercial kits (Quantikine, R&D Systems, MN, USA).

Glucose Tolerance Test

Glucose tolerance is assessed by oral administration of glucose (1 gram per kilogram body weight). Blood drawn from the tail is measured for glucose at 0', 15', 30', 60', 90', 120' and 180'. Glucose levels are measured with Elite glucose test strips and a glucometer.

Hepatic MRI Measurement of Fat Content

Hepatic fat content is measured using a double-echo chemical shift gradient-echo magnetic resonance imaging (MRI) sequence that provides in-phase and opposed-phase images in a single acquisition for assessment/quantification of fat in mouse liver. The T1-weighted opposed-phase MR imaging technique is sensitive for detection of relatively small amounts of tissue fat. MRI images are performed with a 1.5-T system (Sigma LX; GE, Milwaukee, USA). Double-echo MR imaging is performed with a repetition time (TR) of 125 msec, double echo times (TEs) of 4 and 6.5 msec, and a flip angle of 80°. Imaging parameters include section thickness of 3 mm, 13-cm field of view, 256*160 matrix, and one signal acquired, with use of a knee coil. Transverse (axial) and coronal images are acquired at the level of the liver with a 3 mm section thickness and no intersection gap. Quantitative assessment of signal intensity (SI) measurements of SI changes between in-phase and opposed-phase images is computed as described in previous reports [Mitchell, D. G, et al., Invest. Radiol 26:1041-1052 (1991); Tomohiro, N. et al., Radiology 218:642-646 (2001)]. The SI index was calculated as follows: SI index=$(SI_{ip}-SI_{op})/SI_{ip}$, where $SI_{ip}$ is SI on in-phase images and $SI_{op}$ is SI on opposed-phase images. The SI index reflects the fraction of SI loss on opposed phase images compared with the SI on in-phase images.

Experimental Analysis for Immune-Mediated Hepatitis Model

Liver Enzymes

Sera from individual mice were obtained and serum aspartate aminotransferase (AST) and alanine aminotransferase (ALT) levels were measured by an automatic analyzer.

Histological Examination

Hematoxylin/eosin staining of paraffin-embedded liver sections is performed. Sections are examined by two experienced pathologists that are blinded to the experiment conditions.

PC-12 Cell Culture

PC-12 cells are grown in Dulbecco's modified Eagle's medium (DMEM) supplemented with 5% fetal calf serum, 10% horse serum, 100 µg/ml streptomycin, and 100 U/ml penicillin. The cultures are maintained in an incubator at 37° C. in a humidified atmosphere of 5% $CO_2$. $5 \times 10^4$ cells/ml are cultured in 24-well plates. Cells are subjected to neurotoxins and neuroprotection tests as described below.

Treatment of PC-12 with Neurotoxins

For Aβ toxicity, Aβ(25-35) peptide (1-2 µM final concentration) is incubated for 10 minutes at 37° C. before added to cells.

For cholesterol toxicity 5 µM cholesterol are added to the medium. *Serum-free cytotoxicity is tested growing the cells in the medium without serum supplement.

Induction of Experimental Colitis 2,4,6-trinitrobenzene sulfonic acid (TNBS) (Sigma)—colitis is induced by intrarectal installation of TNBS, 1 mg/mouse, dissolved in 100 ml of 50% ethanol as described [Collins, C., et al., Eur. J. Immunol. 26:3114-3118 (1996)].

Clinical Assessment of Colitis

Diarrhea is followed daily throughout the study.

Macroscopic Score of Colitis

Colitis assessment is performed 14 days following colitis induction using standard parameters [Madsen, K. L., et al., Gastroenterology 113:151-159 (1997); Trop, S., et al., Hepatology 27:746-755 (1999)].

Four macroscopic parameters are determined, namely: degree of colonic ulcerations, intestinal and peritoneal adhesions, wall thickness and degree of mucosal edema. Each parameter is graded on a scale from 0 (completely normal) to 4 (most severe) by two experienced blinded examiners.

Grading of Histological Lesions

For histological evaluation of inflammation, distal colonic tissue (last 10 cm) is removed and fixed in 10% formaldehyde. Five paraffin sections from each mouse are then stained with hematoxyllin-eosin by using standard techniques. The degree of inflammation on microscopic cross sections of the colon is graded semiquantitatively from 0 to 4 [Madsen et al., (1997) ibid.; Trop et al., Hepatology 27:746-755 (1999)]. Grade 0: normal with no signs of inflammation; Grade 1: very low level of leukocyte infiltration; Grade 2: low level of leukocyte infiltration; and Grade 3: high level of infiltration with high vascular density, and bowel wall thickening; Grade 4: transmural infiltrates with loss of goblet cells, high vascular density, wall thickening, and disruption of normal bowel architecture. The grading is performed by two experienced blinded examiners.

Splenic and Hepatic Lymphocyte Isolation

Splenocytes and intrahepatic lymphocytes were isolated as follows, livers and spleens were kept in RPMI-1640+FCS then spleens were crushed through 70 µm nylon cell strainer (Falcon) and centrifuged (1250 rpm for 7 min) for the removal of debris. Red blood cells were lysed with 1 ml of cold 155 mM ammonium chloride lysis buffer and immediately centrifuged (1250 rpm for 3 min). Splenocytes were then washed and resuspended with 1 ml RPMI+FCS. Remains of connective tissue were removed. The viability by trypan blue staining was above 90%. For intrahepatic lymphocytes, livers were first crushed through a stainless mesh (size 60, Sigma) and the cell suspension was placed in a 50-ml tube for 5 min so cell debris will descend. 10 ml of Lymphoprep (Ficoll, Axis-Shield PoC AS, Oslo, Norway) was slowly placed under the same volume of cell suspension in 50-ml tubes. The tubes were then centrifuged at 1800 rpm for 18 min. Cells in the interface were collected and moved to new tubes which were centrifuged again at 1800 rpm for 10 min, to obtain a pellet of cells depleted of hepatocytes to a final volume of 250 µl. Approximately $1 \times 10^6$ cells/mouse liver, were recovered.

Both splenocytes and liver-associated lymphocytes are isolated from all animals in all experimental groups.

Model for PD

The neurotoxin 6OHDA (8 µM/rat) is stereotaxically injected in 4 µl into the right substantia nigra of male Sprague-Dawley rats (weighing 250-270 g), for induction of nigral lession. This animal model show PD-related clinical symptoms within 3 days following 6OHDA injection.

Stepping Adjustments Test

The number of stepping adjustments is counted for each forelimb during slow sideway movements in forehand and backhand directions over a standard flat surface. The stepping adjustments test is repeated three times for each forelimb.

Forelimb-Placing Test

The forelimb-placing test assesses the rats' ability to make directed forelimb movements in response to a sensory stimulus. Rats are held with their limbs hanging unsupported. They are then raised to the side of a table so that their wiskers make contact with the top surface while the length of their body parallels the edge of the tabletop. Control rats place their forelimb on the tabletop in response to whisker stimulation almost every time, whereas injured rats do not. Each test includes 10 trials of placement of each forelimb and is repeated daily for three consecutive days. The results of both tests are expressed as percentage of forelimb stepping adjustments and placing in the lesioned side, as compared with the nonlesioned side. ANOVA analysis of repeated measures is used to determine significant differences in the motor performance.

At the end of experiment striata of the animals are collected, and submitted to HPLC analysis for the presence of dopamine and its metabolites 3,4-dihydroxyphenylacetic acid (DOPAC), and homovanillic acid (HVA). The levels of dopamine and metabolites in the lesioned side of the treated animals (relative to the nonlesioned side) are compared to the non-treated animals.

In addition, in some of the animal's brain sections are submitted to immunohistochemistry analysis for tyrosine hydroxylase (TH), a rate-limiting enzyme for dopamine synthesis, which serves as an important marker of dopaminergic cell loss.

Model for ALS

Transgenic mice expressing the human G93A SOD1 (B6SJL-TgN[SOD1-G93A]1Gur), are used. These tg mice model show ALS related clinical symptoms starting at about 14-15 weeks of age, and die at about 18-20 weeks.

Mice are treated with different concentrations of synthetic β-glycolipid derivatives such as the compounds of Formula II, III and IV, in drinking water, starting at week 8 of age (N=7), versus non-treated mice as controls (N=6).

"Rotarod" Motor Function Test

Mice are weekly tested for motor function using a "Rotarod" device (Panlab, Barcelona) to detect onset and progression of disease-related weakness. The mice are placed on a rotating cylinder with a constant rate of acceleration. When the mice can no longer continue running and fall from the cylinder, the total time they spend on the cylinder and final speed achieved is recorded electronically, thus allowing calculation of the total distance run. Each mouse performs three rotarod trials, and the best performance each week is recorded. A "baseline" distance is established at 12 weeks of age to which subsequent performance is compared. Onset of disease-related weakness is defined as a sustained decrease of more than 30% of baseline maximum running distance. Survival is defined by an accepted artificial endpoint as the time at which the mouse is no longer able to right itself within 30 seconds of being placed on its side.

A clinical 5-point score is used for assessing the ability to move:
4=normal mobility; 3=movement with limited use of the hindlegs; 2=movement with the use of the forelegs; 1=movement only for a short period with the use of the forelegs; and 0=unable to move.

The time to onset and death/survival of treated and control groups are compared using Kaplen-Meier curve analysis (using SPS 12 for Windows®). ANOVA analysis of repeated measures is used to determine significant differences in the motor performance.

EXAMPLE 1

Synthesis of β-Glycolipid Analogs

Three synthetic novel analogs of β glycolipids, namely AD2897, AD2898, and AD2899, were synthesized using the following protocols:

AD2897-N-adamantyl-N'-glucosylsphingosine thiourea also indicated as Formula II, was synthesized as follows:
50 mg of β-Glucosylsphingosine were "dissolved" in 50 ml of 0.5N carbonate buffer pH=9. 21 mg 1-Adamantyl isothiocyanate in 30 ml of 0.5N carbonate buffer pH=9 were added. The mixture was stirred overnight at room temperature, evaporated to dryness and the residue dissolved in dichloromethane/methanol, 2:1 (50 ml). 30 ml 0.5N HCl were then added slowly and the mixture transferred to a reparatory funnel. The upper phase was removed and another amount of 30 ml HCl was added. The product was washed with a $3^{rd}$ amount of HCl and then twice with $H_2O$. The organic phase was dried on $MgSO_4$, filtered and evaporated to dryness in a rotavapor. The product was then purified by silica gel column chromatography using increasing concentrations of methanol in dichloromethane. The fractions containing the pure compound (as indicated by HPLC) were pooled and evaporated to dryness. The residue was suspended in $H_2O$ and lyophilized to obtain a 50% yield.

AD2898-Octyl-sulfonamido-glucosylsphingosine, (Glucosylsphingosine-octylsulfonamide) also indicated as Formula III, was synthesized as follows:
Two mg β-Glucosylsphingosine were dissolve in a mixture of 5 ml Ethanol and 5 ml 0.5N carbonate buffer pH=10.1 mg octane sulfonylchloride was added. The mixture was stirred overnight at room temperature, then evaporated to dryness and the residue dissolved in dichloromethane/methanol, 2:1 (5 ml). 3 ml 0.5N $NaHCO_3$ were added slowly and the mixture transferred to a small separatory funnel. The upper phase removed and another amount of 3 ml $NaHCO_3$ was added. The product was washed with a $3^{rd}$ amount of sodium bicarbonate and then twice with $H_2O$. The organic phase was dried on $MgSO_4$, filtered and evaporated to dryness by a stream of nitrogen. The product was purified by silica gel column chromatography using increasing concentrations of methanol in dichloromethane. The fraction containing the pure compound (as indicated by HPLC) was evaporated to dryness. The residue was suspended in $H_2O$ and lyophilized.

AD2899: Hexadecyl-sulfonamido-glucosylsphingosine, (Glucosylsphingosine-hexadecylsulfonamide) also indicated as Formula IV, was synthesized as follows:

Two mg β-Glucosylsphingosine were dissolve in a mixture of 5 ml Ethanol and 5 ml 0.5N carbonate buffer pH=10.1 mg hexadecanoylsulfonyl chloride was added. The mixture was stirred overnight at room temperature, then evaporated to dryness and the residue dissolved in dichloromethane/methanol, 2:1 (5 ml). 3 ml 0.5N $NaHCO_3$ were added slowly and the mixture transferred to a small separatory funnel. The upper phase removed and another amount of 3 ml $NaHCO_3$ was added. The product was washed with a $3^{rd}$ amount of sodium bicarbonate and then twice with $H_2O$. The organic phase was dried on $MgSO_4$, filtered and evaporated to dryness by a stream of nitrogen. The product was purified by a silica gel column chromatography using increasing concentrations of methanol in dichloromethane. The fraction containing the pure compound (as indicated by HPLC) was evaporated to dryness. The residue was suspended in $H_2O$ and lyophilized.

The analogs were formulated in solvent containing 15% Cremophor EL/15% ethanol/70% PBS, prior to use.

EXAMPLE 2

Effect of Novel Synthetic β-glycolipids on ConA Induced Immune Mediated Hepatitis To determine the clinical and immunological effect of the novel synthetic compounds of the invention, immune-mediated hepatitis was examined using the ConA induced hepatitis model. Therefore, the different synthetic and natural derivatives of β-glycolipids of Formula II, III and IV (AD2897, AD2898, and AD2899, respectivelly), were examined using seven groups of C57Bl/6 mice, as summarized by Table 1. Mice in experimental groups A-G (eight mice in each group) were injected with ConA. Group A mice were administered with 100 μl intraperitoneal injection of solvent only [15% Cremophor EL/15% ethanol/70% PBS](C:E). Mice in groups B, C, D, E, F, and G were administered with intraperitoneal injection of 1 μg or 10 μg of each of the three analogs Formulated in solvent as described in Experimental Procedures. Animals were sacrificed and examined.

In order to evaluate the potential beneficial effect of the three novel analogues of the invention on immune-mediated hepatitis, the effect of treatment with two concentrations of the three synthetic analogs on liver damage in all tested groups was assessed by determination of serum aspartate aminotransferase (AST), and alanine aminotransferase (ALT) levels.

As clearly shown by FIG. 1, both ALT and AST levels decreased in animals treated using either AD2897 or AD2898 as synthetic analogs, with the former requiring the administration of a 10 μg dosage and the later only a 1 μg dosage. As these liver transaminases provide evidence for hepatic cell injury their decrease in the serum suggest the alleviation of liver damage and immune mediated liver injury.

Assessment of the effect of any of the synthetic analogs on the immune response was next determined by analysis of the cytokine serum level of IFNγ in each animal using a commercial "sandwich" ELISA kit, and by FACS analysis of intrahepatic and intrasplenic (peripheral) lymphocytes levels.

Figure 2:
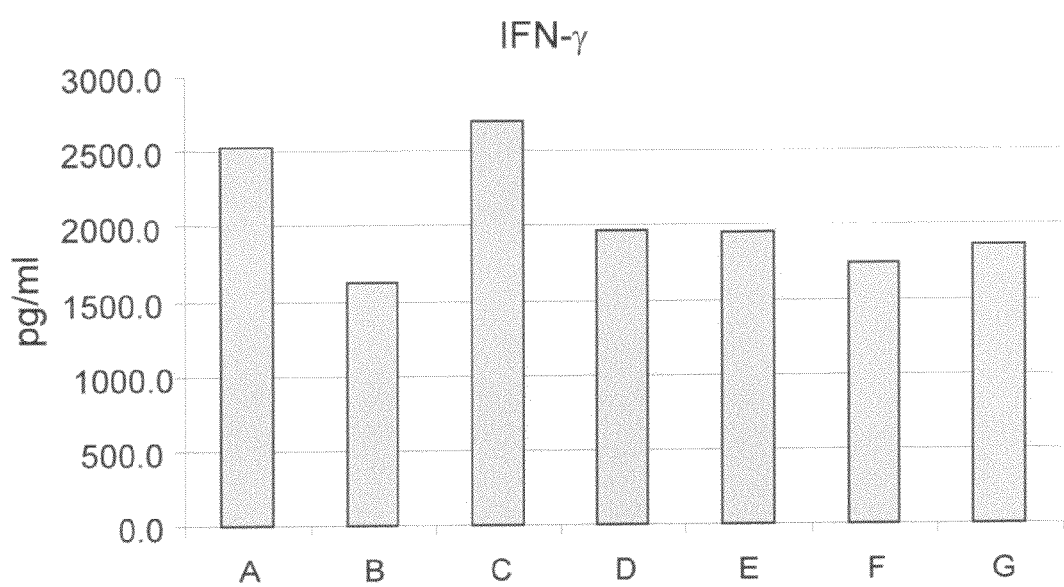
FIG. 2 The effect of administration of β glycolipids synthetic analogs of the invention upon serum IFNγ levels in a ConA induced hepatitis model. Mice experimental groups are indicated in Table 1. A-control, B+C (AD2897 1 µg and 10 µg/mice), D+E (AD2898 1 µg and 10 µg/mice), F+G (AD2899 1 µg and 10 µg/mice).

As shown by FIG. 2, mice treated with either AD2898 or AD2899 in both high and low dosages or with a low dosage of AD2897, exhibited a decrease in IFNγ serum levels, suggesting a negative effect upon this pro-inflammatory cytokine.

Figure 3:
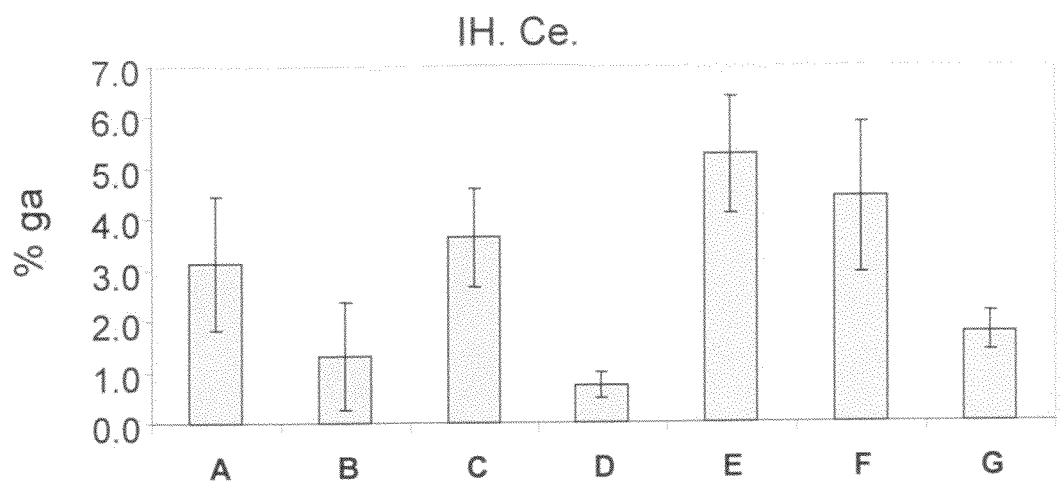
FIG. 3 The effect of administration of 1 µg or 10 µg/mice dosage regimes of β glycolipids synthetic analogs of the invention (AD2897, AD2898, and AD2899) upon intrahepatic NKT cell levels in a ConA induced hepatitis model. Abbreviations: IH (Intrahepatic); ce (cells); ga. (gated).
Figure 4:
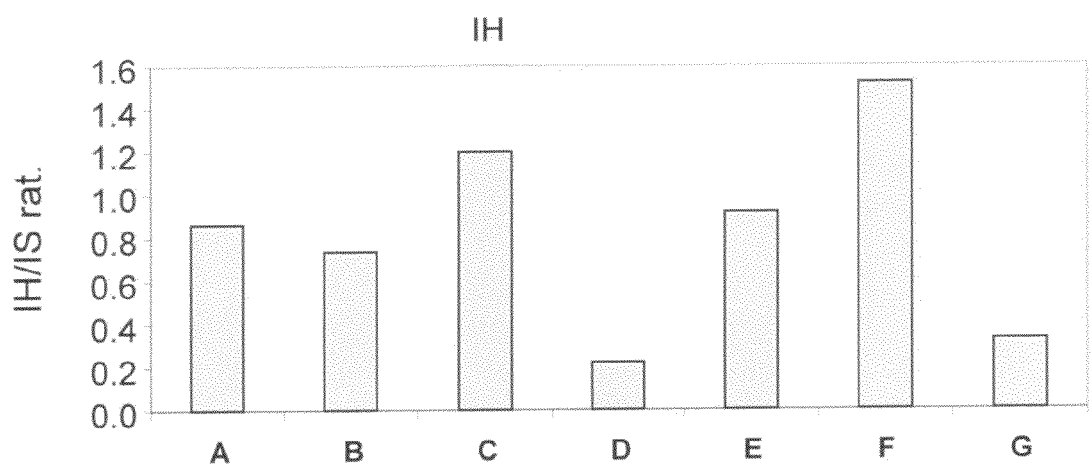
FIG. 4 Histogram depicting the effect of administration of 1 µg or 10 µg/mice dosage regimes of the β glycolipids synthetic analogs of the invention (AD2897, AD2898, and AD2899) upon the ratio of peripheral/intrahepatic NKT cells in ConA induced hepatitis mice. Abbreviations: IH (Intrahepatic); IS (intraspleenic); rat. (ratio).
Figure 5:
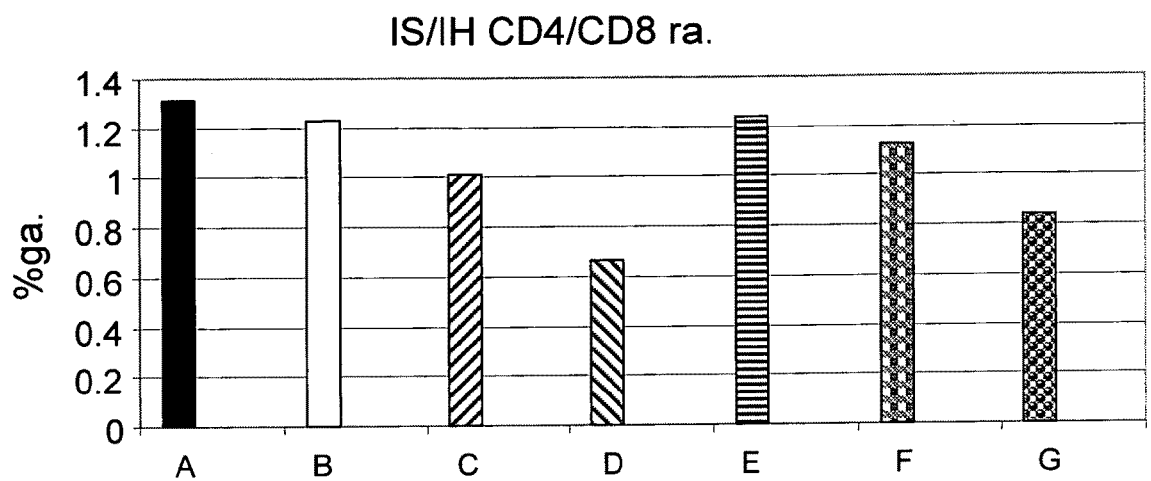
FIG. 5 Histogram comparing the effect of 1 µg or 10 µg/mice regimes of the β glycolipids synthetic analogs of the invention (AD2897, AD2898, and AD2899) upon the ratio of peripheral/intrahepatic CD4:CD8 ratio. Abbreviations: IH (Intrahepatic); IS (intraspleenic); rat. (ratio).

Treatment of animals with a low dosage of the AD2897 analog, a low dosage of the AD2898 analog or a high dosage of the AD2899 analog resulted in a decrease in intrahepatic NKT cell levels and a decrease in the intrahepatic/peripheral ratio of these lymphocytes (FIGS. 3 and 4). A similar corresponding increase was observed in the peripheral/intrahepatic ratio of the CD4/CD8 ratio (FIG. 5).

Taken together these results indicate that the three novel sysnthetic β-glycolipids analogs of the invention, AD2897, AD2898, and AD2899 (Formula II, III and IV, respectivelly) are capable of exerting an immunomodulatory effect upon the immune system of animals suffering from immune mediated liver injury.

TABLE 1

| Group: | Treatment |
|---|---|
| A | Con A (C: E) |
| B | AD2897 1 μg/mice |
| C | AD2897 10 μg/mice |
| D | AD2898 1 μg/mice |
| E | AD2898 10 μg/mice |
| F | AD2899 1 μg/mice |
| G | AD2899 10 μg/mice |

EXAMPLE 3

Use of the Compounds of Formula II, III and IV for Treatment of Immune Mediated Colitis To determine the clinical and immunological effect of administration of different synthetic and natural derivatives of β-glycolipids such as the compounds of Formula II, III and IV, on a murine model of experimental colitis, eight groups of C57Bl/6 mice, consisting of 10 mice each, are studied. Table 2 summarizes the experimental groups. Colitis is induced by intracolonic installation of trinitrobenzenesulfonic acid (TNBS) on day 1 and 5 in groups A-D. Group A mice are fed regular chow diet. Group B-D mice receive oral (PO) daily of the compounds of Formula II, III and IV, respectively. Groups E-G mice are not treated with TNBS, but receive oral (PO) daily amount of the compounds of Formula II, III and IV, respectively, and serve as control groups.

Mice are followed for macroscopic and microscopic colitis scores. The immunomodulatory effect of GC is determined by FACS analysis of intrahepatic and intrasplenic lymphocytes for NKT, CD4 and CD8 markers, and by measurement of serum IFNγ, IL2, IL12, IL4 and IL10 cytokine levels.

TABLE 2

| Group: | Treatment: |
|---|---|
| A | TNBS |
| B | TNBS with OP compound of Formula I |
| C | TNBS with OP compounds of Formula II |
| D | TNBS with OP compounds of Formula III |
| E | TNBS with OP compounds of Formula I |
| F | OP compounds of Formula II |
| G | OP compounds of Formula III |
| H | OP PBS |

EXAMPLE 4

Synergistic Effect for Different Mixtures of the Compounds of Formula II, III and IV in the Treatment of Immune Mediated Colitis To determine the possible immuno-modulation effect of different mixtures of the different synthetic derivatives of β-glycolipids, the effect of mixtures of the compounds of Formula II, III and IV is tested using a murine model of colitis.

As summarized in Table 3, seven groups of mice are studied, each consisting of 10 mice. Colitis is induced by intracolonic installation of trinitrobenzenesulfonic acid (TNBS) on day 1 and 5 in groups A to D. Group A mice are fed regular chow diet. Groups B and E mice receive oral (PO) daily amount of a mixture of the compounds of Formula II and III, groups C and F receive a mixture of the compounds of Formula II and IV, groups D and G mice receive oral (PO) daily amount of a mixture of the compounds of Formula III and IV. Groups E to G mice are not treated with TNBS, but receive oral (PO) daily amount of a mixture of Groups B and E mice receive oral (PO) daily amount of a mixture of the compounds of Formula II, III and IV, as described above, and serve as control groups.

Mice are followed for macroscopic and microscopic colitis scores, as well as for survival and functional status and weight.

TABLE 3

| Group: | Treatment: |
|---|---|
| A | TNBS |
| B | TNBS with compounds of Formula II and III (1:1) |
| C | TNBS with compounds of Formula II and IV |
| D | TNBS with compounds of Formula III and IV |
| E | compounds of Formula II and III (1:1) |
| F | compounds of Formula II and IV |
| G | compounds of Formula III and IV |

The immune modulatory effect of beta-glycolipids is determined by FACS analysis of intrahepatic and intrasplenic lymphocytes for NKT, CD4 and CD8 markers, and by measurement of serum cytokine levels.

EXAMPLE 5

Different Mixtures of Compounds of Formula I, II and III in Colitis-Determination of Different Mixture Ratios To test different combinations of the different synthetic β-glycolipids derivatives, and to identify the most effective mixture combination, different quantitative ratio of the compounds of Formula II, III and IV are checked (1:1, 1:10, and 1:100), using the murine model of colitis.

As summarized in Table 4, sixteen groups of C57BL mice are studied, each consisting of 10 mice. Colitis is induced by intracolonic installation of trinitrobenzenesulfonic acid (TNBS) on day 1 and 5 in all groups. Group A mice are fed regular chow diet. Groups B-F mice receive oral (PO) daily amount of a mixture of the compounds of Formula II and III in different ratio, groups G-K receive a mixture of the compounds of Formula II and IV in different ratio and groups L-P receive a mixture of the compounds of Formula III and IV in different ratio as indicated by the table.

Mice are followed for macroscopic and microscopic colitis scores, as well as for different cell populations by FACS: CD4, CD8, NKT in spleen and liver (not pooled), and for serum cytokines IFNγ and IL4 by ELISA.

TABLE 4

| Group | Day 1 and 5 | Day 1-9 feeding |
|---|---|---|
| A | TNBS 0.5 mg × 2 | — |
| B | TNBS 0.5 mg × 2 | Compounds of Formula II and III (1:1) |
| C | TNBS 0.5 mg × 2 | Compounds of Formula II and III (1:10) |
| D | TNBS 0.5 mg × 2 | Compounds of Formula II and III (1:100) |
| E | TNBS 0.5 mg × 2 | Compounds of Formula III and II (1:10) |
| F | TNBS 0.5 mg × 2 | Compounds of Formula III and II (1:100) |
| G | TNBS 0.5 mg × 2 | Compounds of Formula II and IV (1:1) |
| H | TNBS 0.5 mg × 2 | Compounds of Formula I and III (1:10) |
| I | TNBS 0.5 mg × 2 | Compounds of Formula II and IV (1:100) |
| J | | Compounds of Formula IV and II (1:10) |
| K | | Compounds of Formula IV and II (1:100) |
| L | | Compounds of Formula III and IV (1:1) |
| M | | Compounds of Formula III and IV (1:10) |
| N | | Compounds of Formula III and IV (1:100) |
| O | | Compounds of Formula IV and III (1:10) |
| P | | Compounds of Formula IV and III (1:100) |

EXAMPLE 6

Use of the Compounds of Formula II, III and IV for the Treatment of Immune Hepatocellular Carcinoma The immunomodulatory effect of different synthetic derivatives of β-glycolipids and particularly of the compounds of Formula II, III and IV, demonstrated by the ConA induce hepatitis model, encouraged the inventors to further investigate other immune-related disorders, such as hepatocellular carcinoma (HCC). Therefore, the clinical and immunological consequences of administration of the compounds of Formula I, II and III on hepatocellular carcinoma (HCC) are next examined, using mice transplanted with human Hep3B HCC. Four groups of athymic Balb/c mice, consisting of 8 mice each, are sublethally irradiated and transplanted with human Hep3B HCC, followed by daily intraperitoneal injections of the compounds of Formula II, III and IV, (in 100 μl PBS) or PBS (100μ) for 25 days. Animals are followed for tumor size and weight and for intrahepatic and intrasplenic lymphocyte subpopulations, serum cytokine levels and expression of STAT1, STAT4 and STAT6 in splenocytes. The different test groups are summarized in Table 5.

TABLE 5

| Group: | Treatment: |
|---|---|
| A | Hep3B HCC, the compound of Formula II |
| B | Hep3B HCC, the compound of Formula III |
| C | Hep3B HCC, the compound of Formula IV |
| D | Hep3B HCC, PBS control |

EXAMPLE 7

Effect of Mixtures of β-glycolipids on the Treatment of Immune Hepatocellular Carcinoma The inventors further analyze the effect of different combinations of synthetic derivatives of β-glycolipids, and particularly of mixtures of the compounds of Formula II, III and IV, which are shown effective in the ConA hepatitis model, by using the murine HCC model.

Athymic Balb/c mice (n=8/group) are sublethally irradiated and transplanted with human Hep3B HCC, followed by daily intraperitoneal injections of PBS, the compounds of Formula II+III, II+IV and III+IV (in 100 μl PBS, groups A, B, C and D, respectively) for 25 days. Animals are followed for serum α-fetoprotein (AFP) and for intrahepatic and intrasplenic lymphocyte subpopulations.

EXAMPLE 8

The Compounds of Formula II, II and IV for the Treatment of Non Alcoholic Steatohepatitis (NASH)

Effect of the Compounds of Formula II, III and IV and Mixtures Thereof on Diabetes To evaluate the effect of different synthetic derivatives of β-glycolipids and mixtures thereof on diabetes, fourteen groups of C57bl mice, consisting of 12 mice each are studied. Groups A-G mice are ob/ob mice, whereas Groups H-N are C57bl mice. Groups A-G and Groups I-N mice are injected intraperitoneally with the following compounds in 100 μl PBS every other day for 14 days: the compound of Formula II (groups B, I), compound of Formula III (groups C, J), compound of Formula IV (groups D, K), and a mixture of the compounds of Formula II and III (groups E, L), mixture of the compounds of Formula II and IV (groups F, M) and mixture of the compounds of Formula III and IV (groups G, N). Group A and Group H naïve ob/ob mice and naïve C57bl mice, respectively, are left untreated and serve as controls.

On the 14$^{th}$ day, glucose tolerance tests are performed on 6 mice from each group.

Effect of Orally Administered Compounds of Formula II, III and IV and Mixtures Thereof on NASH To evaluate the effect of different synthetic derivatives of β-glycolipids and mixtures thereof on the various metabolic and immunologic components of the NASH model, 14 groups of C57bl mice, consisting of 12 mice each are studied. Groups A-G mice are ob/ob mice, whereas Groups H-N are C57bl mice. Groups A-G and Groups I-N mice receive for 14 days oral daily amount of the following synthetic derivatives of β-glycolipids: the compound of Formula II (groups B, I), compound of Formula III (groups C, J), compound of Formula IV (groups D, K), and a mixture of the compounds of Formula II and III (groups E, L), mixture of the compounds of Formula II and IV (groups F, M) and mixture of the compounds of Formula III and IV (groups G, N). Group A and Group H naïve ob/ob mice and naïve C57bl mice, respectively, are left untreated and serve as controls.

On the 14$^{th}$ day, glucose tolerance tests are performed on 6 mice from each group.

The Effect of Synthetic Derivatives of β-Glycolipids on the Hepatic Fat Content

To determine the effect of synthetic derivatives of β-glycolipids and mixtures thereof on hepatic fat content, 14 groups of C57bl mice, consisting of 12 mice each are studied. Groups A-G mice are ob/ob mice, whereas Groups H-N are C57bl mice. Groups A-G and Groups I-N mice are injected intraperitoneally every other day for 14 days with the following synthetic derivatives of β-glycolipids: the compound of Formula I (groups B, I), compound of Formula III (groups C, J), compound of Formula IV (groups D, K), and a mixture of the compounds of Formula II and III (groups E, L), mixture of the compounds of Formula II and IV (groups F, M) and mixture of the compounds of Formula III and IV (groups G, N). Group A and Group H naïve ob/ob mice and naïve C57bl mice, respectively, are left untreated and serve as controls.

To determine hepatic fat content, mice of all test groups undergoing an abdominal MRI on day 14 of the experiment. Hepatic fat content is determined and described as the SI index IP-OP/IP. Liver size, in area, is also determined.

EXAMPLE 9

Mixed Synthetic Derivatives of β-Glycolipids in Diabetic Pssammomys Model

To determine the effect of different combinations of synthetic derivatives of β-glycolipids, and particularly of the compounds of Formula II, III and IV as well as of mixtures thereof, on diabetes, metabolic syndrome and hepatic steatosis, the diabetic Passamon model is used. The sand rat (Psammomys obesus), a model of nutritionally-induced type II diabetes, develops significant hyperinsulinemia, hyperglycemia and hypertriglyceridemia on a high-energy diet. Seven groups of five-month-old sand rats on high energy diets are studied (n=10 per group). Animals are treated by daily intraperitoneal injections of the compound of Formula I (group A), the compound of Formula III (group B), the compound of Formula IV (group C), a mixture of the compounds of Formula II+III (group D), a mixture of the compounds of Formula II+IV (group E), a mixture of compounds of Formula III+IV (group F) or PBS (group G), for 25 days. On day 25, all psammomys are sacrificed and examined.

Determination of hepatic fat content and inflammation is performed by magnetic resonance imaging (MRI), examination of liver biopsies and measurement of serum Alanine aminotransferase (ALT) and Aspartate aminotransferase (AST) levels. Body weight and post prandial serum glucose, insulin, triglyceride and free fatty acid (FFA) levels are assessed. To determine the mechanism of the effect of these derivatives on the Th1/Th2 balance, expression of the transcription factors STAT1, STAT4, STAT5 and STAT6 is determined in splenocytes.

EXAMPLE 10

The Effect of Synthetic Derivatives of β-Glycolipids on Non Alcoholic Fatty Liver Disease (NAFLD) and the Metabolic Syndrome Using the Diabetic Cohen Rat Model To determine the effect of mixtures of different synthetic derivatives of β-glycolipids on diabetes, hepatic steatosis and metabolic syndrome, the Cohen rat model is used by the inventors. The Cohen rat is a lean, non-insulin resistant model of type 2 diabetes that features zone 1 and 2 mixed micro and macrovesicular steatosis and elevated serum transaminases.

Seven groups of Cohen rats are studied (n=10/group). Animals are treated by daily intraperitoneal injections of the compound of Formula II (group A), the compound of Formula III (group B), the compound of Formula IV (group C), a mixture of the compounds of Formula II+III (group D), a mixture of the compounds of Formula II+IV (group E), a mixture of compounds of Formula III+IV (group F) or PBS (group G), for 45 days. Assessment of NAFLD is performed by MR imaging, examination of liver biopsies and measurement of serum transaminases. Metabolic follow up parameters included body weight, oral glucose tolerance test (OGTT), serum lipids and pancreatic histology. Immune modulation is assessed by FACS analysis of intrahepatic and intrasplenic lymphocytes.

EXAMPLE 11

Examination of the Neuroprotective Effect of Synthetic Derivatives of β-Glycolipids and Combinations Thereof Against Aβ Peptide (Model of AD) in PC12 Neuronal Cell Cultures In order to establish a reliable cell culture system for screening the neuroprotective effect of different potential synthetic derivatives of β-glycolipids, and particularly of the compounds of Formula II, III and IV, the neurotoxic effect of Aβ (25-35), cholesterol and serum-free conditions is first examined in PC-12 cell model.

PC-12 cell culture is a rat pheochromocytoma cell line, which displays phenotypic characteristics of sympathetic neurons. In the past decade, different cellular and molecular experiments have shown that PC-12 cells are an excellent in vitro model for investigating various neurological disorders, such as Alzheimer's disease and Parkinson's disease.

PC-12 cells die in a dose dependent manner in response to exposure to the AD-related Aβ peptide. These cells also suffer from the neurotoxic effects when coming in contact with high cholesterol levels, or under serum-deprivation conditions. On the other hand, these cells benefit from the neuroprotective effect of statins, vitamin E and vitamin C after exposure to the neurotoxic effect of Aβ peptide.

PC-12 cell culture is therefore, a convenient model to test neurotoxicity and to detect neuroprotective drugs capable of overcoming the effects of such toxic conditions. The neuroprotective effect of different tested compounds on neuronal cells cultured in the presence of Aβ peptide neurotoxic is reflected by the increment of the neuronal cell survival.

The capability of the PC-12 cells to exhibit neurotoxic as well as neuroprotective effects makes these cells an authentic model for studying and screening for new neuroprotective drugs.

The inventors are thus demonstrating the neuroprotective effect of administration of synthetic derivatives of β-glycolipids such as the compounds of Formula II, III and IV and of different combinations thereof, against the neurotoxic condition induced by the AD related Aβ peptide in PC-12 neuronal cell culture. The efficacy of treatment with the compounds of Formula II, III and IV is estimated by assessing the percentage of PC-12 cell survival after being exposed to the Aβ (25-35) peptide toxic conditions.

Therefore, PC-12 cells are treated with different concentrations of the compounds of Formula I, II and III ranging between 0.01 to 1000 microgram per ml.

Cell survival (%) is calculated relative to control cells not exposed to the Aβ peptide or to different synthetic compounds of the invention.

EXAMPLE 12

Examination of the Neuroprotective Effect of Different Synthetic Derivatives of β-Glycolipids and Combinations Thereof Against 3-NP (Model of HD), MPTP and 6-OHDA (Models of PD), and Glutamate (Model of ALS) in PC12 Neuronal Cell Cultures The neuroprotective effect of synthetic derivatives of β-glycolipids in neuronal-cell model encourages their use in the prevention and treatment of AD, and possibly other neurodegenerative disorders.

In order to assess the potential neuroprotective effect of the compounds of Formula II, III and IV on other neurodegenerative disorders, the rescue of PC-12 cells treated with different neurotoxins (presenting different neurodegenerative disorders) is next tested by the inventors.

For examining the applicability of different synthetic derivatives of β-glycolipids for the treatment of PD, PC12 cells exposed to 6-hydroxydopamine (6OHDA) or to 1-methyl-4-phenyl-1,2,3,6-tetrahydropyridine (MPTP), as neurotoxins, are treated with different concentrations of the compounds of Formula II, III and IV ranging between 0.01 to 1000 microgram per ml.

Treatment of PC12 cells exposed to 3-nitropropionic acid (3-NP) as a neurotoxin, with different concentrations of the compounds of Formula II, III and IV ranging between 0.01 to 1000 microgram per ml, reflects the feasibility of treating HD with synthetic derivatives of β-glycolipids.

For evaluating the potential neuroprotective effect of synthetic derivatives of β-glycolipids on the ALS model, PC12 cells exposed to glutamate as a neurotoxin, are treated with different concentrations of the compounds of Formula II, III and IV ranging between 0.01 to 1000 microgram per ml, cell survival is then calculated.

EXAMPLE 13

Effect of β-Glycolipids Effect on AD Symptoms Using a AD-Animal Model

In order to examine the feasibility of using different synthetic derivatives of β-glycolipids for the treatment of AD, an in vivo animal model is used. Transgenic mice model expressing a mutation in the amyloid precursor protein (APP) and in the presenilin1 gene, is used as AD model by the inventors. Mice are treated with different concentrations of the compounds of Formula II, III and IV in different modes of delivery such as, drinking water, gavage, and i.p. injection. The treated animals are then evaluated for improvement in clinical parameters.

EXAMPLE 14

Effect of Different Synthetic Derivatives of β-Glycolipids on PD Symptoms Using a PD-Animal Model The inventors next evaluate the neuroprotective effect of administration of different synthetic derivatives of β-glycolipids such as the compounds of Formula II, III and IV and of different combinations thereof on Parkinson's disease using an animal model. Rats stereotaxically injected with 6OHDA into the right substantia nigra develop PD-related motor deficits starting 3 days following injection. Rats are treated with different concentrations of the compounds of Formula II, III and IV in different modes of delivery such as drinking water, gavage, and i.p. injection. The treated animals are then evaluated for improvement in the motor deficits using the stepping and placing tests.

EXAMPLE 15

Effect of Different Synthetic Derivatives of β-Glycolipids on ALS Onset and Death in an ALS-Animal Model The neuroprotective effect of different synthetic derivatives of β-glycolipids on AD and PD, encouraged the inventors to evaluate the feasibility of using these drugs for the treatment of another neurodegenerative disease, ALS. Therefore, ALS tg mice (starting at 8 weeks of age) are treated with synthetic derivatives of β-glycolipids such as the compounds of Formula II, III and IV and of different combinations thereof. The effect is evaluated by measuring performance in the rotarod as described in Experimental procedures, by evaluating disease development using clinical score and by examining the survival of the animals.

EXAMPLE 16

Effect of Different Synthetic Derivatives of β-Glycolipids on Acute Experimental Autoimmune Encephalomyelitis (EAE)

The significant immunomodulatory effect of different synthetic derivatives of β-glycolipids and their potential neuroprotective effect in cell culture and animal models is further explored by the inventors for investigating their potential neuroprotective effect in animal models for diseases of the central nervous system (CNS). Therefore, the inventors examine the effect of the compounds of Formula II, III and IV on experimental autoimmune encephalomyelitis (EAE), an autoimmune inflammatory disease resulting in demyelination of the white matter in the CNS. In many of its clinical and histopathological aspects, EAE resembles human multiple sclerosis (MS) and acute disseminating encephalomyelitis. EAE can be induced in genetically susceptible animals by a single s.c. injection of myelin associated antigens, such as myelin oligodendrocyte glycoprotein (MOG), or proteolipid protein (PLP), emulsified in CFA and followed by a booster with *Bordetella pertussis*. A characteristic monophasic paralytic disease develops 10-13 days later. EAE serves as a useful experimental model for investigating new therapeutic strategies in MS. Various immunosuppressive agents are found effective in prevention and treatment of EAE, including corticosteroids and copolymer 1. However, patients are so far treated either symptomatically or with immunosuppressive agents, and no satisfactory therapy for MS has as yet been established.

Two mouse models are used for analyzing the potential effect of different synthetic derivatives of β-glycolipids for the treatment of EAE, C57Bl mice immunized with MOG (myelin oligodendrocyte glycoprotein), and SJL mice immunized with PLP (proteolipid protein) are treated with different concentrations of the compounds of Formula II, III and IV and of different combinations thereof.

While this invention has been described in terms of some specific examples, many modifications and variations are possible. It is therefore understood that within the scope of the appended claims, the invention may be realized otherwise than as specifically described.

The invention claimed is:

1. A compound of Formula (I):

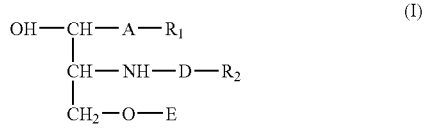

wherein
A represents —CH=CH—;
D represents —CSNH—, —CS—, or —SO$_2$—;
E represents a β-glycosyl radical selected from glucosyl, galactosyl, sulfated galactosyl, mannosyl, or lactosyl;
R$_1$ is a linear C$_{8-21}$ alkyl; and
R$_2$ is adamantanyl;
or pharmaceutically acceptable salts thereof.

2. The compound according to claim 1, wherein D is —CS— or —SO$_2$.

3. The compound according to claim 1, wherein said E is glucosyl.

4. The compound according to claim 1, wherein said R$_1$ is a C$_{10-16}$alkyl.

5. The compound according to claim 2, wherein R$_1$ is C$_{13}$ alkyl.

6. The compound according to claim 1, having Formula II:

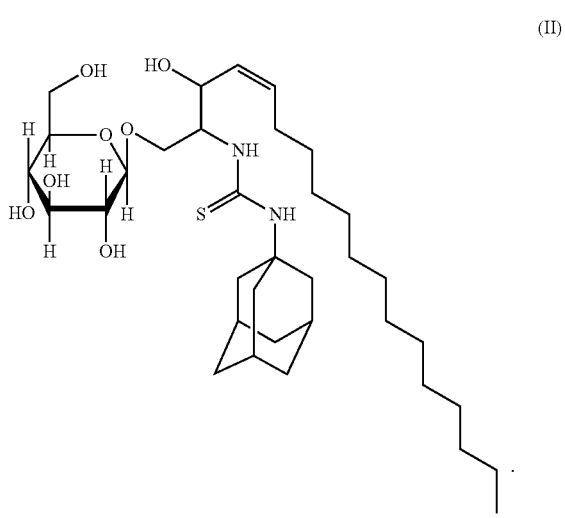

7. A composition comprising the compound of claim 1 in a pharmaceutically acceptable carrier, diluent, excipient and/or additive.

8. A composition comprising the compound of claim 6 in a pharmaceutically acceptable carrier, diluent, excipient and/or additive.

9. A therapeutic composition for the treatment of a pathologic condition in a mammalian subject comprising as an active ingredient any one of:
(a) at least one of the compounds of claim 1 or claim 6;
(b) a mixture of at least two compounds of claim 1;
(c) educated NKT cells pre-exposed to any one of the compounds of claim 1 or claim 6, or to any mixture or any combination thereof; or
(d) any combination of (a), (b) or (c);
wherein said composition optionally further comprises at least one of a pharmaceutically acceptable carrier, diluent, excipient and/or additive, and
wherein said pathologic condition is metabolic syndrome, diabetes, immune-mediated hepatitis, immune-mediated colitis, immune-mediated hepatocellular carcinoma, melanoma, non-alcoholic steatohepatitis, HIV infection, HCV infection or HBV infection.

10. The therapeutic composition according to claim 9, comprising a mixture of at least one of the compounds of (a) and a second β-glycolipid, wherein said at least one of the compounds and said second β-glycolipid are at a mass ratio between 1:1 to 1:1000.

11. The therapeutic composition according to claim 9, wherein said composition modulates the Th1/Th2 cell balance in a subject suffering from said pathologic condition.

12. A method for the preparation of a medicament for the treatment of a pathologic condition in a subject in need thereof comprising the steps of:
- (A) providing an immunomodulatory composition comprising any one of:
    - a. at least one of the compounds of claim 1 or claim 6;
    - b. a mixture of at least two compounds of claim 1 or claim 6;
    - c. educated NKT cells pre-exposed to any one of the compounds of claim 1 or claim 6, or to any mixture or any combination thereof; and
    - d. any combinations of (a), (b) and (c); and
- (B) admixing the immunomodulatory compound provided in step (A) into a pharmaceutically acceptable carrier, wherein the pathologic condition is metabolic syndrome, diabetes, immune-mediated hepatitis, immune-mediated colitis, immune-mediated hepatocellular carcinoma, melanoma, non-alcoholic steatohepatitis, HIV infection, HCV infection or HBV infection.

13. A method for the treatment or amelioration of a pathologic condition in a mammalian subject in need thereof comprising the step of administering to said subject a therapeutically effective amount of the therapeutic composition of claim 9, wherein the pathologic condition is metabolic syndrome, diabetes, immune-mediated hepatitis, immune-mediated colitis, immune-mediated hepatocellular carcinoma, melanoma, non-alcoholic steatohepatitis, HIV infection, HCV infection or HBV infection.

14. The method according to claim 13, wherein said administering comprises a mixture of at least one of the compounds of claim 1 or claim 6 and a second β-glycolipid, wherein said at least one of the compounds and said second β-glycolipid are at a mass ratio between 1:1 to 1:1000.

15. The method according to claim 13, comprising modulating the Th1/Th2 cell balance towards a Th2 anti-inflammatory or a Th1 pro-inflammatory response.

16. The method according to claim 13, wherein said administering step comprises oral, intravenous, intramuscular, subcutaneous, intraperitoneal, parenteral, transdermal, intravaginal, intranasal, mucosal, sublingual, topical, rectal, or subcutaneous administration, or any combination thereof.

* * * * *